(12) United States Patent
Bankiewicz et al.

(10) Patent No.: US 8,309,355 B2
(45) Date of Patent: Nov. 13, 2012

(54) METHODS OF TREATING PARKINSON'S DISEASE USING VIRAL VECTORS

(75) Inventors: Krys Bankiewicz, Garrett Park, MD (US); Janet Cunningham, Alameda, CA (US)

(73) Assignees: Genzyme Corporation, Framingham, MA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 12/384,935

(22) Filed: Apr. 10, 2009

(65) Prior Publication Data

US 2010/0104537 A1   Apr. 29, 2010

Related U.S. Application Data

(60) Division of application No. 11/102,521, filed on Apr. 8, 2005, now Pat. No. 7,534,613, which is a continuation of application No. 09/887,854, filed on Jun. 21, 2001, now Pat. No. 6,953,575, which is a continuation of application No. 09/320,171, filed on May 26, 1999, now Pat. No. 6,309,634.

(60) Provisional application No. 60/134,748, filed on May 18, 1999, provisional application No. 60/086,949, filed on May 27, 1998.

(51) Int. Cl.
*C12N 15/63* (2006.01)
*C12N 5/00* (2006.01)
*A01N 63/00* (2006.01)
*A01N 43/04* (2006.01)
*A61K 48/00* (2006.01)

(52) U.S. Cl. ............ 435/455; 435/320.1; 424/93.2; 424/93.21; 424/93.6; 514/44

(58) Field of Classification Search .............. 435/455, 435/320.1; 424/93.2, 93.21, 93.6; 514/44
See application file for complete search history.

(56) References Cited

U.S. PATENT DOCUMENTS

| | | | |
|---|---|---|---|
| 4,916,151 A * | 4/1990 | Bey et al. .................. 514/419 |
| 5,139,941 A | 8/1992 | Muzyczka et al. |
| 5,173,414 A | 12/1992 | Lebkowski et al. |
| 5,399,346 A | 3/1995 | Anderson et al. |
| 5,599,706 A * | 2/1997 | Stinchcomb et al. ......... 435/366 |
| 5,677,158 A | 10/1997 | Zhou et al. |
| 5,720,720 A | 2/1998 | Laske et al. |
| 6,045,807 A | 4/2000 | Gage et al. |
| 6,103,226 A | 8/2000 | Kang et al. |
| 6,180,613 B1 | 1/2001 | Kaplitt et al. |
| 6,503,888 B1 * | 1/2003 | Kaplitt et al. ............. 514/44 R |
| 6,953,575 B2 | 10/2005 | Bankiewicz et al. |

FOREIGN PATENT DOCUMENTS

| | | |
|---|---|---|
| DE | 3841955 A1 | 7/1989 |
| WO | WO 95/28493 A1 | 10/1995 |
| WO | WO 95/34670 A2 | 12/1995 |
| WO | WO 97/17458 A1 | 5/1997 |
| WO | WO 98/00014 A1 | 1/1998 |
| WO | WO 95/05864 A1 | 3/1998 |

OTHER PUBLICATIONS

Castro et al., 2001, Histl. Histopathol., vol. 16, p. 1225-1238.*
Patent Abstracts of Japan vol. 013, No. 328, Jul. 24, 1989.
Bankiewicz, et al., "Practical Aspects of the Development of Ex Vivo and in Vivo Gene Therapy for Parkinsons Disease," *Exp Neurol* 144:147-156 (1997).
Bankiewicz, et al., "Application of Gene Therapy for Parkinsons Desease: Nonhuman Primate Experience," *Adv Pharmaco* 142:801-806 (1998).
Brynes, et al., "Immunological Instability of Persistant Adenovirus Vectors in the Brain:Peripheral Exposure to Vector Leads to Renewed Inflammation, Reduced Gene Expression, and Demyelination,"*J Neurosci* 16(9):3045-3055 (1996).
Carter, "Adeno-Associated Virus Vectors," *Curr Opin Biotechnol* 3:533-539 (1992).
Chen, et al., "Varibles Affecting Convection-Enhanced Delivery ti the Striatum: A Systematic Examination of Rate Infusion, Cannula Size, Infusate Concentration, and Tissue Cannula Sealing Time,"*J Neurosurg* 90:315-320 (1999).
Chen, et al., "Surface properties, more than size, limiting convective distribution of virus-sized particles and viruses in the central nervous system," *J Neurosurg* 103:311-319 (2005).
Conrad, et al., "Safety of Single Dose Administration of an Adeno-Associated Viruse (AAV)-CFTR Vector in the Primate Lung," *Gene Ther* 3:658-668 (1996).
Deonarain, "Ligand-targeted receptor-mediated vectors for gene delivery," *Exp Opin Ther Patents* 8(1):53-69 (1998).
During, et al., "In Vivo Expression of Therapeutic Human Genes for Dopamine Production in the Caudates of MPTP-Treated Monkeys Using an AAV Vector," *Gene Ther* 5:820-827 (1998).
Eberling, et al., "A Novel MPTP Primate Model of Parkinsons Disease: Neurochemical and Clinical Changes," *Brain Res* 805:259-262 (1998).
Eck, et al., "Goodman & Gilma's The Pharmacological Basis of Therapeutics," Mcgraw-Hill, New York, pp. 77-101.
Edge, et al., "Total Synthesis of a Human Leukocytelnterferon Gene," *Nature* 292:756-762 (1981).

(Continued)

*Primary Examiner* — Shin-Lin Chen
(74) *Attorney, Agent, or Firm* — Robins Law Group

(57) ABSTRACT

Methods of delivering viral vectors, particularly recombinant AAV virions, to the central nervous system (CNS) are provided for the treatment of CNS disorders, particularly those disorders which involve the neurotransmitter dopamine. The methods entail providing rAAV virions that comprise a transgene encoding aromatic amino acid decarboxylase (AADC) and administering the virions to the brain of a mammal using a non-manual pump.

12 Claims, 9 Drawing Sheets

OTHER PUBLICATIONS

Fan, et al., "Behavioral Recovery in 6-Hydroxydopamine-Lesioned Rats by Cotransduction of Striatum with Tyrosine Hydroxylase and Aromatic L-Amino Acid Decarboxylase genes Using Two Separate Adeno Associated Virus Vectors," *Hum Gene Ther* 9:2527-2535 (1998).

Flotte, et al., "Stable in Vivo Expression of the Cystic Fibrosis Transmembrane Conductance Regulator With an Adeno-Associated Virus Vector," *PNAS* 90:10613-10617 (1993).

French, "Human Gene Therapy," *Nature* 392:25-30 (1998).

Gardlik, et al., "Vectors and Delivery Systems in Gene Therapy," *Med Sci Monit* 11(4):RA110-RA121 (2005).

Gorecki, "Prospects and Problems of Gene Therapy: An Update," *Exp Opin Emerging Drugs* 6(2):187-198 (2001).

Graham, et al., "Characteristics of a Human Cell Line Transformed by DNA from Human Adenovirus Type 5," *J Gen Virol* 36:59-72 (1977).

Hadaczek, et al., "Convection-Enhanced Delivery of Adeno-Associated Virus Type 2 (AAV2) Into the Striatum and Transport of AAV2 Within Monkey Brain," *Hum Gene Ther* 17:291-302 (2006).

Herzog, et al., Long-Term Correction of Canine Hemophilia B by Gene Transfer of Blood Coagulation Factor IX Mediated by Sdeno-Associated Viral Vector, *Nat Med* 5:56-63 (1999).

Kaplitt, et al., "Long-Term Gene Expression and Phenotypic Correction Using Adeno-Assoicated Virus vectors in the Mammalian Brain," *Nat Genet* 8:148-153 (1994).

Kaplitt, et al., "Transfer and Expression of Potentially Therapeutic Genes into the Mammalian Central Nervous System In Vivo Using Adeno-Associated Viral Vectors," *Viral Vectors, Gene Therapy and Neuroscience Applications*, Kapplitt and Loewy, eds., Academic Press, Sandeigo 12:193-210 (1995).

Kass-Eisler, et al., "The Impact of Developmental Stage, Route od Administration and the Immune System on Adenovirus-Mediated Gene Transfer," *Gene Ther* 1:395-402 (1994).

Kotin, et al., "Prospects for the Use of Adeno-Associated Virus as a Vector for Human Gene Therapy," *Hum Gene Ther* 5:793-801 (1994).

Kroll, et al., "Increasing Volume of Distribution to the Brain with Interstitial Infusion: Dose, Rather Than Convection, Might be the Most Important Factor," *Neurosurgery* 38(4):746-754 (1996).

Langston, "Mechanism of MPTP Toxicity: More Answers, More Questions," *Trends Pharmacol Sci* 6:375-378 (1985).

Leff, et al., "Long-Term Restoration of Striatal L-Aromatic Amino Acid Decarboxylase Activity Using Recombinant Adeno-Associated Viral Vector Gene Transfer in a Rodent Model of Parkinson's Disease," *Neuroscience* 92(1):185-196 (1999).

Leff, et al., *Society for Neuroscience Abstracts* 23(1-2):541 (1997).

Lyden, et al., "Effect of Ischemic Cerebral Volume Changes on Behavior," *Bahavioral Brain Res* 87:59-67 (1997).

Mandel, et al., "Midbrain Injection of Recombiannt Adeno-Associated Virus Encoding Rat Glial Cell Line-Derived Neurotropic Factor Protects Nigral Neurons in a Progressive 6-Hydroxydopamine-Induced Degenerative Model of Parkinsons Disease in Rats," *PNAS* 94:14083-14088 (1997).

Mandel, et al., "Characterization of Intranastriatal Recombinant Adeno-Associated Virus-Mediated Gene Transfer of Human Tyrosine Hydroxylase and Human GTP-Cyclohydrolase I in a Rat Model of Parkinsons Disease," *J Neurosci* 18(11):4271-4284 (1998).

Matsushita, et al., "Adeno-Associated Virus Vectors can be Efficiently Produced Without Helper Virus," *Gene Ther* 5:938-945 (1998).

Mizuno, et al., "Adeno-Associated Virus Vector Containing the Herpes Simplex Virus Thymidine Kinase Gene Causes Complete Regression of Intracerebrally Implanted Human Gilomas in Mice, In Conjunction with Ganciclovir Administration," *Jpn J Cancer Res* 89:76-80 (1998).

Moffat, et al., "L-Dopa and Dopamine-Producing Gene Cassettes for Gene Therapy Approaches to Parkinsons Disease," *Exp Neurol* 144:69-73 (1997).

Muzyczka, "Use of Adeno-Associated Virus as a General Transduction Vector for Mammalian Cells," *Curr Topics Microbial and Immunol* 158:97-129 (1992).

Okada, et al., Gene Therapy Against an Experimental Glioma Using Adeno-Associated Virus Vectors, *Gene Therapy* 3:957-964 (1996).

Passini, et al., "Gene Delivery to the Mouse Brain With Adeno-Associated Virus," *Methods in Molecular Biology* 246:225-236 (2004).

Ross, et al., "Gene Therapy in the United States: A Five Year Status Report," Hum Gene Ther 7:1781-1790 (1996).

Samulski, et al., "A Recombinant Plasmid From Which an Infectious Adeno-Associated Virus. Genome can be Excised in Vitro and its Use to Study Viral Replication," J Virol 61(10):3096-3101 (1987).

Szczypka, et al., "Viral Gene Delivery Selectively Restores Feeding and Prevents Lethality of Dopamine-Deficient Mice," Neuron 22:167-178 (1999).

Verma, et al., "Gene Therapy-Promises, Problems and Prospects," *Nature* 389:239-242 (1997).

Vite, et al., "Adeno-Associated Virus Vector-Mediated Transduction in the Cat Brain," *Gene Ther* 10:1874-1881 (2003).

Xiao, et al., "Gene Transfer by Adeno-Associated Virus Vectors Into the Central Nervous System," *Exp Neurol* 144:113-124 (1997).

Yang, et al., "Immune Responses to Viral Antigens Versus Transgene Product in the Elimination of Recombinant Adenovirus-Infected Hepatocytes In Vivo," *Gene Ther* 127-144 (1996).

Yang, et al., "Cellular Immunity to Viral Antigens Limits E1-Deleted Adenoviruses for Gene Therapy," *PNAS* 91:4407-4411 (1994).

Zhu, et al., "A Continuous Intracerebral Gene Delivery System for In Vivo Liposome-Mediated Gene Therapy," *Gene Ther* 3(6):472-476 (1996).

\* cited by examiner

SEQUENCE LISTING

<160> NUMBER OF SEQ ID NOS: 12

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence:primer/probe
      145A

<400> SEQUENCE: 1
aagtcatcgg ctcgggtacg tagacgatat c                              31

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:primer/probe
      tk -continued

```
<400> SEQUENCE: 2
atagcagcta caatccagct accattctgc                                     30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:primer/probe
      145A

<400> SEQUENCE: 3
gctcggtacc cgggcggagg ggtggagtcg                                     30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:primer/probe
      145B

<400> SEQUENCE: 4
taatcattaa ctacagcccg gggatcctct                                     30

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:primer/probe
      P547

<400> SEQUENCE: 5
ggtttgaacg agcgctcgcc atgc                                           24

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:primer/probe
      blunt 1

<400> SEQUENCE: 6
cgcgccgata tcgttaacgc ccgggcgttt aaacagcgct gg                       42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence:primer/probe
      blunt 2

<400> SEQUENCE: 7
cgcgccagcg ctgtttaaac gcccgggcgt taacgatatc gg                       42

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence:primer/probe
      5DIVE2
```

```
<400> SEQUENCE: 8
tgtggtcacg ctgggggggg gggcccgagt gagcacg                           37

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence:primer/probe
      polylinker 1

<400> SEQUENCE: 9
ccgctacagg gcgcgatatc agctcactca a                                 31

<210> SEQ ID NO 10
<211> LENGTH: 58
<212> TYPE: DNA
<213> ORGANISM: Artificial Sequence
<220> FEATURE:
<223> OTHER INFORMATION: Description of Artificial Sequence:primer/probe
      polylinker 2

<400> SEQUENCE: 10
ggatccggta ccgcccgggc tctagaatcg atgtatacgt cgacgtttaa accatatg    58

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence:primer/probe
      E4.1

<400> SEQUENCE: 11
agaggcccgg gcgttttagg gcggagtaac ttgc                              34

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:primer/probe
      E4.2

<400> SEQUENCE: 12
acatacccgc aggcgtagag ac                                           22
```

METHODS OF TREATING PARKINSON'S DISEASE USING VIRAL VECTORS

CROSS-REFERENCE TO RELATED APPLICATIONS

This application is a divisional of U.S. patent application Ser. No. 11/102,521, filed Apr. 8, 2005, which is a continuation of U.S. patent application Ser. No. 09/887,854, filed Jun. 21, 2001, now U.S. Pat. No. 6,953,575, which is a continuation of U.S. patent application Ser. No. 09/320,171, filed May 26, 1999, now U.S. Pat. No. 6,309,634, which is related to U.S. Provisional Patent Application No. 60/134,748, filed May 18, 1999, and U.S. Provisional Patent Application No. 60/086,949, filed May 27, 1998, from which applications priority is claimed under 35 USC §119(e)(1), and which applications are incorporated herein by reference in their entireties.

REFERENCE TO GOVERNMENT RIGHTS

Part of this work was made under the auspices of the U.S. Department of Energy, at the University of California/Lawrence Berkeley National Laboratory, under CRADA No. BG98039 and DOE Contract No. DE-AC03-76SF00098, now Contract No. DE-AC02-05CH11231. The government has certain rights in this invention.

FIELD OF THE INVENTION

The present invention relates generally to efficient delivery of viral vectors to the CNS. More particularly, the present invention relates to gene therapy for the treatment of central nervous system (CNS) disorders, particularly those disorders which involve the neurotransmitter dopamine.

BACKGROUND OF THE INVENTION

CNS disorders are major public health issues. Parkinson's disease (PD) alone affects over 1 million people in the United States. Clinically, PD is characterized by a decrease in spontaneous movements, gait difficulty, postural instability, rigidity and tremor. Parkinson's disease is caused by the degeneration of the pigmented neurons in the substantia nigra of the brain, resulting in decreased dopamine availability. Altered dopamine metabolism has also been implicated in schizophrenic patients who show increased dopamine in certain areas of the brain. Currently, many CNS disorders such as PD are treated by systemic administration of a therapeutic agent. Systemic administration, however, is often inefficient because of a drug's inability to pass through the blood brain barrier and because many drugs cause peripheral side effects. Thus, many potentially useful compounds, such as proteins, cannot be administered systemically. If these compounds are successful in penetrating the blood-brain-barrier, they may also induce central nervous system side effects as well. Treatment of PD currently involves oral administration of the dopamine-precursor, L-dopa often in combination with a compound such ascarbidopa, a peripheral inhibitor of the enzyme aromatic amino acid decarboxylase (AADC) that decarboxylates dopa to dopamine. In the majority of patients, however, production of AADC in the affected brain regions is reduced as PD progresses and, consequently, larger and larger doses of L-dopa are required, leaving the patients with reduced therapeutic benefits and increased side effects.

In view of the limitations of current systemic therapies, gene delivery is a promising method for the treatment for CNS disorders such as PD. A number of viral based systems for gene transfer purposes have been described, such as retroviral systems which are currently the most widely used viral vector systems for this purpose. For descriptions of various retroviral systems, see, e.g., U.S. Pat. No. 5,219,740; Miller and Rosman (1989) *BioTechniques* 7:980-990; Miller, A. D. (1990) *Human Gene Therapy* 1:5-14; Scarpa et al. (1991) *Virology* 180:849-852; Burns et al. (1993) *Proc. Natl. Acad. Sci. USA* 90:8033-8037; and Boris-Lawrie and Temin (1993) *Cur. Opin. Genet. Develop.* 3:102-109.

Adeno-associated virus (AAV) systems are emerging as the leading candidates for use in gene therapy. AAV is a helper-dependent DNA parvovirus which belongs to the genus *Dependovirus*. AAV requires infection with an unrelated helper virus, either adenovirus, a herpesvirus or vaccinia, in order for a productive infection to occur. The helper virus supplies accessory functions that are necessary for most steps in AAV replication. For a review of AAV, see, e.g., Berns and Bohenzky (1987) *Advances in Virus Research* (Academic Press, Inc.) 32:243-307.

AAV infects a broad range of tissue, and has not elicited the cytotoxic effects and adverse immune reactions in animal models that have been seen with other viral vectors. (see, e.g., Muzyczka, (1992) *Current Topics in Microbiol. and Immunol.* 158:97-129; Flotte et al. (1993) *PNAS USA* 90:10613-10617; Kass-eiser et al. (1992) *Gene Therapy* 1:395-402; Yange et al. *PNAS USA* 91:4407-4411; Conrad et al. (1996) *Gene Therapy* 3:658-668; Yang et al. (1996) *Gene Therapy* 3:137-144; Brynes et al. (1996) *J. Neurosci.* 16:3045-3055). Because it can transduce nondividing tissue, AAV may be well adapted for delivering genes to the central nervous system (CNS). U.S. Pat. No. 5,677,158 described methods of making AAV vectors. AAV vectors containing therapeutic genes under the control of the cytomegalovirus (CMV) promoter have been shown to transduce mammalian brain and to have functional effects in models of disease.

AAV vectors carrying transgenes have been described, for example, in Kaplitt et al (1994) *Nature Genetics* 8:148-153; WO 95/28493 published 26 Oct. 1995; WO 95/34670, published 21 Dec. 1995; During et al., (1998) *Gene Therapy* 5:820-827; Mandel et al. (1998) *J. Neurosci.* 18:4271-4284; Szczypka et al. (1999) *Neuron* 22:167-178.). However, delivery of AAV vectors to the CNS has proven difficult. AAV has been used to transfer the thymidine (tk) kinase gene to experimental gliomas in mice, and the ability of AAV-tk to render these brain tumors sensitive to the cytocidal effects of ganciclovir has been demonstrated. Okada et al. (1996) *Gene Therapy* 3:959-964; Mizuno et al. (1998) *Jpn. J. Cancer Res.* 89:76-80. Infusion of an AAV-CMV vector containing the human tyrosine hydroxylase (TH) gene, an enzyme involved in conversion of the amino acid tyrosine to dopa, into adult rat brain resulted in transduction of both neurons and glia (Kaplitt et al. (1995) VIRAL VECTORS, GENE THERAPY AND NEUROSCIENCE APPLICATIONS, Kaplitt and Loewy eds., 12:193-210, Academic Press, San Diego; Bankiewicz et al. (1997) *Exper. Neurol.* 144:147-156). Delivery of the same vector to monkey striatum resulted in robust expression of TH for up to 2.5 months (During et al., supra). Furthermore, AAV-CMV-TH was tested in a rodent model of Parkinson's Disease where it caused significant improvement in rotational behavior of 6-hydroxydopamine-lesioned rats (Fan et al. (1998) *Human Gene Therapy* 9:2527-2537; Mandel et al. (1997) *PNAS USA* 94:14083-14088).

However, while reports such as these demonstrate AAV's potential for targeting the CNS, they also demonstrate that direct injection of AAV vectors into the CNS results in limited numbers of transfected cells and that the transfected cells are clustered in a narrow area near the injection tracts. (see, e.g., During et al, supra; Fan et al., supra). Since multiple injections into the CNS cause undesirable complications, there remains a need for methods of delivering AAV vectors to larger areas of the brain using the least number of injection sites. In addition, the relationship between dose of injected vector and its resulting distribution in brain tissue has not been previously reported.

Furthermore, gene therapy of PD has focused on delivery of at least two genes encoding enzymes involved in dopamine synthesis, namely TH and AADC. These methods are subject to all of the delivery problems discussed above and, in addition, require that both genes are expressed in the proper amounts. Thus, treatment of PD using AAV-AADC in combination with L-dopa has also not been demonstrated.

SUMMARY OF THE INVENTION

In one aspect, the present invention provides methods for delivering recombinant AAV (rAAV) virions carrying a transgene to the central nervous system (CNS) of a subject, for example a human, using convection-enhanced delivery (CED). CED can be conducted, for example, using either an osmotic pump or an infusion pump. In a preferred embodiment, the transgene encodes an aromatic amino acid decarboxylase (AADC) or active fragment thereof. When the transgene encodes an AADC, it is preferable to administer the rAAV virions into the striatum of the CNS.

In another aspect, the invention provides for methods for delivering recombinant AAV virions to a subject having a CNS disorder. The rAAV virions encode a suitable therapeutic polypeptide and are administered into the CNS of the subject using CED. In a preferred embodiment, the CNS disorder is Parkinson's disease (PD), the rAAV virions are administered into the striatum of the CNS, and the nucleic acid sequence encodes AADC.

In another aspect, methods for treating a neurodegenerative disease in a subject are provided. A preparation of recombinant adeno-associated virus (rAAV) virions carrying a therapeutic nucleic acid sequence that is expressible in transduced cells is administered to the CNS using convection-enhanced delivery (CED). In one embodiment, the neurodegenerative disease is PD and the therapeutic polypeptide is an AADC. In yet another embodiment, the method of treating the neurodegenative disease also includes administering at least one additional therapeutic compound to the subject, for example, systemically administering L-dopa and, optionally, carbidopa.

In yet another aspect, methods of determining levels of dopamine activity in the CNS of subject are provided. A labeled tracer is administered to the subject. The tracer is preferably a compound that binds to a cell which utilizes dopamine and the label is preferably a radioisotope, for instance, 6-[$^{18}$F]-fluoro-L-m-tyrosine ($^{18}$F-FMT). The detection of the label is indicative of dopamine activity via binding of the tracer. Preferably, the subject's CNS is imaged, for example using positron emission tomography (PET) scanning.

These and other embodiments of the subject invention will readily occur to those of ordinary skill in the art in view of the disclosure herein.

BRIEF DESCRIPTION OF THE DRAWINGS

FIGS. 4a and b show expression of tk in neurons. FIGS. 4c and d show expression in neurons and glial near the site of osmotic pump infusion.

DETAILED DESCRIPTION OF THE INVENTION

Figure 1A:
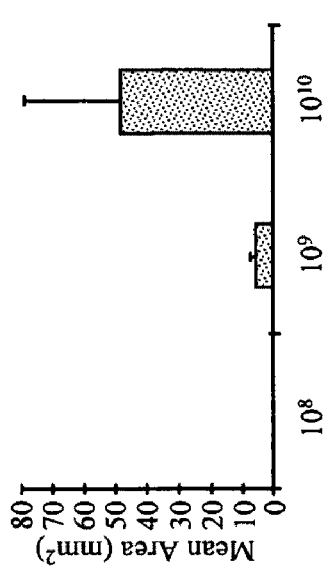
FIG. 1, panels a though d, depict dose responses (expression of the AAV-tk transgene) in rat following intracranial infusion pump delivery. The tissue volume (FIG. 1a); mean area (FIG. 1b); length (FIG. 1c) and number of cells (FIG. 1d) expressing the transgene are depicted.

The practice of the present invention will employ, unless otherwise indicated, conventional methods of virology, microbiology, molecular biology and recombinant DNA techniques within the skill of the art. Such techniques are explained fully in the literature; See, e.g., Sambrook, et al. *Molecular Cloning: A Laboratory Manual* (Current Edition); *Current Protocols in Molecular Biology* (F. M. Ausubel, et al. eds., current edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijessen, ed.); *Fundamental Virology*, 2nd Edition, vol. I & II (B. N. Fields and D. M. Knipe, Eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

DEFINITIONS

In describing the present invention, the following terms will be employed, and are intended to be defined as indicated below.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsidating a heterologous nucleotide sequence of interest which is flanked on both sides by AAV ITRs. A rAAV virion is produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties, such as a nucleotide integration vector and other nucleic acid molecules, into suitable host cells.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

A "gene" refers to a polynucleotide containing at least one open reading frame that is capable of encoding a particular polypeptide or protein after being transcribed or translated. Any of the polynucleotide sequences described herein may be used to identify larger fragments or full-length coding sequences of the genes with which they are associated. Methods of isolating larger fragment sequences are know to those of skill in the art.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

The term "aromatic amino acid decarboxylase" or "AADC" refers to a polypeptide which decarboxylates dopa to dopamine. Thus, the term includes a full-length AADC polypeptide, active fragments or functional homologues thereof.

A "functional homologue," or a "functional equivalent" of a given polypeptide includes molecules derived from the native polypeptide sequence, as well as recombinantly produced or chemically synthesized polypeptides which function in a manner similar to the reference molecule to achieve a desired result. Thus, a functional homologue of AADC encompasses derivatives and analogues of those polypeptides—including any single or multiple amino acid additions, substitutions and/or deletions occurring internally or at the amino or carboxy termini thereof—so long as integrity of activity remains.

Techniques for determining nucleic acid and amino acid "sequence identity" or "homology" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 90%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, Supra.

"Convection-enhanced delivery" refers to any non-manual delivery of agents. In the context of the present invention, examples of convection-enhanced delivery (CED) of AAV can be achieved by infusion pumps or by osmotic pumps.

The term "central nervous system" or "CNS" includes all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. The "cranial cavity" refers to the area underneath the skull (cranium). Regions of the CNS have been associated with various behaviors and/or functions. For example, the basal ganglia of the brain has been associated with motor functions, particularly voluntary movement. The basal ganglia is composed of six paired nuclei: the caudate nucleus, the putamen, the globus pallidus (or pallidum), the nucleus accumbens, the subthalamic nucleus and the substantia nigra. The caudate nucleus and putamen, although separated by the internal capsula, share cytoarchitechtonic, chemical and physiologic properties and are often referred to as the corpus striatum, or simply "the striatum." The substantia nigra, which degenerates in Parkinson's patients, provides major dopaminergic input into the basal ganglia.

The terms "subject", "individual" or "patient" are used interchangeably herein and refer to a vertebrate, preferably a mammal. Mammals include, but are not limited to, murines, simians, humans, farm animals, sport animals and pets.

An "effective amount" is an amount sufficient to effect beneficial or desired results. An effective amount can be administered in one or more administrations, applications or dosages.

The term "labeled tracer" refers to any molecule which can be used to follow or detect a defined activity in vivo, for example, a preferred tracer is one that binds to cells that are utilizing dopamine. Preferably, the labeled tracer is one that can be viewed in a whole animal, for example, by positron emission tomograph (PET) scanning or other CNS imaging techniques. Suitable labels include, but are not limited to radioisotopes, fluorochromes, chemiluminescent compounds, dyes, and proteins, including enzymes.

GENERAL OVERVIEW OF THE INVENTION

Central to the present invention is the development of methods which allow for the efficient delivery of viral vectors, such as AAV, into the CNS of animal. Previously, researchers have had only minimal success delivering viral vectors to widespread areas of the brain. Using convection-enhanced delivery devices (for example, osmotic or infusion pumps), viral vectors can be delivered to many cells over large areas of the brain. Moreover, the delivered vectors efficiently express transgenes in CNS cells (e.g., neurons or glial cells).

Using the methods of viral vector delivery described herein, novel gene therapy treatments for CNS disorders (e.g., Parkinson's Disease) can be devised. In one embodiment, Parkinson's disease (PD) is treated by combining systemic L-dopa and/or carbidopa therapy with CNS-administration (e.g., via CED) of AAV vectors carrying a transgene encoding AADC, an enzyme involved in dopamine metabolism.

Advantages of the invention, include, but are not limited to (i) efficient and widespread delivery of viral vectors (such as AAV) to the CNS; (ii) expression of nucleic acids (e.g., transgenes) carried by the viral vectors; (iii) identification of a therapeutic regime for Parkinson's Disease that involves delivery of one transgene in combination with administration of a pro-drug; and (iv) the ability to non-invasively monitor CNS gene therapy using PET scan.

Construction of Viral Vectors

Gene delivery vehicles useful in the practice of the present invention can be constructed utilizing methodologies well known in the art of molecular biology (see, for example, Ausubel or Maniatis, supra). Typically, viral vectors carrying transgenes are assembled from polynucleotides encoding the transgene(s), suitable regulatory elements and elements necessary for production of viral proteins which mediate cell transduction. For example, in a preferred embodiment, adeno-associated viral (AAV) vectors are employed.

General Methods

A preferred method of obtaining the nucleotide components of the viral vector is PCR. General procedures for PCR are taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, $Mg^{2+}$ and ATP concentration, pH, and the relative concentration of primers, templates and deoxyribonucleotides. Exemplary primers are described below in the Examples. After amplification, the resulting fragments can be detected by agarose gel electrophoresis followed by visualization with ethidium bromide staining and ultraviolet illumination.

Another method for obtaining polynucleotides is by enzymatic digestion. For example, nucleotide sequences can be generated by digestion of appropriate vectors with suitable recognition restriction enzymes. The resulting fragments can then be ligated together as appropriate.

Polynucleotides are inserted into vector genomes using methods well known in the art. For example, insert and vector DNA can be contacted, under suitable conditions, with a restriction enzyme to create complementary or blunt ends on each molecule that can pair with each other and be joined with a ligase. Alternatively, synthetic nucleic acid linkers can be ligated to the termini of a polynucleotide. These synthetic linkers can contain nucleic acid sequences that correspond to a particular restriction site in the vector DNA. Other means are known and available in the art.

Retroviral and Adenoviral Vectors

A number of viral based systems have been used for gene delivery. For example, retroviral systems are known and generally employ packaging lines which have an integrated defective provirus (the "helper") that expresses all of the genes of the virus but cannot package its own genome due to a deletion of the packaging signal, known as the psi sequence. Thus, the cell line produces empty viral shells. Producer lines can be derived from the packaging lines which, in addition to the helper, contain a viral vector which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.) Representative retroviral vectors include but are not limited to vectors such as the LHL, N2, LNSAL, LSHL and LHL2 vectors described in e.g., U.S. Pat. No. 5,219,740, incorporated herein by reference in its entirety, as well as derivatives of these vectors, such as the modified N2 vector described herein. Retroviral vectors can be constructed using techniques well known in the art. See, e.g., U.S. Pat. No. 5,219,740; Mann et al. (1983) *Cell* 33:153-159.

Adenovirus based systems have been developed for gene delivery and are suitable for delivery according to the methods described herein. Human adenoviruses are double-stranded DNA viruses which enter cells by receptor-mediated endocytosis. These viruses are particularly well suited for gene transfer because they are easy to grow and manipulate and they exhibit a broad host range in vivo and in vitro. For example, adenoviruses can infect human cells of hematopoietic, lymphoid and myeloid origin. Furthermore, adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low level morbidity and are not associated with human malignancies. Accordingly, adenovirus vectors have been developed which make use of these advantages. For a description of adenovirus vectors and their uses see, e.g., Haj-Ahmad and Graham (1986) *J. Virol.* 57:267-274; Bett et al. (1993) *J. Virol.* 67:5911-5921; Mittereder et al. (1994) *Human Gene Therapy* 5:717-729; Seth et al. (1994) *J. Virol.* 68:933-940; Barr et al. (1994) *Gene Therapy* 1:51-58; Berkner, K. L. (1988) *BioTechniques* 6:616-629; Rich et al. (1993) *Human Gene Therapy* 4:461-476.

AAV Expression Vectors

In a preferred embodiment, the viral vectors are AAV vectors. By an "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is bounded (5' and 3') with functional. AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) *Human Gene Therapy* 5:793-801; Berns, K. I. "Parvoviridae and their Replication" in *Fundamental Virology*, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion; deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

Additionally, AAV ITRs may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Suitable DNA molecules for use in AAV vectors will be less than about 5 kilobases (kb) in size and will include, for example, a gene that encodes a protein that is defective or missing from a recipient subject or a gene that encodes a protein having a desired biological or therapeutic effect (e.g., an antibacterial, antiviral or antitumor function). Preferred DNA molecules include those involved in dopamine metabolism, for example, AADC or TH. AAV-AADC and AAV-TH vectors have been described, for example, in Bankiewicz et al. (1997) *Exper't Neurol.* 144:147-156; Fan et al (1998) *Human Gene Therapy* 9:2527-2535 and International Publication WO 95/28493, published Oct. 26, 1995.

The selected nucleotide sequence, such as AADC or another gene of interest, is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

For purposes of the present invention, both heterologous promoters and other control elements, such as CNS-specific and inducible promoters, enhancers and the like, will be of particular use. Examples of heterologous promoters include the CMB promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

The AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988-3996; Vincent et al. (1990) *Vaccines* 90 (Cold Spring Harbor Laboratory Press); Carter, B. J. (1992) *Current Opinion in Biotechnology* 3:533-539; Muzyczka, N. (1992) *Current Topics in Microbiol. and Immunol.* 158:97-129; Kotin, R. M. (1994) *Human Gene Therapy* 5:793-801; Shelling and Smith (1994) *Gene Therapy* 1:165-169; and Zhou et al. (1994) *J. Exp. Med.* 179:1867-1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM $MgCl_2$, 10 mM DTT, 33 ug/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods. See, e.g., Edge, *Nature* (1981) 292:756; Nambair et al. *Science* (1984) 223:1299; Jay et al. *J. Biol. Chem.* (1984) 259:6311.

In order to produce rAAV virions, an AAV expression vector is introduced into a suitable host cell using known techniques, such as by transfection. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Particularly suitable transfection methods include calcium phosphate co-precipitation (Graham et al. (1973) *Virol.* 52:456-467), direct micro-injection into cultured cells (Capecchi, M. R. (1980) *Cell* 22:479-488), electroporation (Shigekawa et al. (1988) *BioTechniques* 6:742-751), liposome mediated gene transfer (Mannino et al. (1988) *BioTechniques* 6:682-690), lipid-mediated transduction (Feigner et al. (1987) *Proc. Natl. Acad. Sci. USA* 84:7413-7417), and nucleic acid delivery using high-velocity microprojectiles (Klein et al. (1987) *Nature* 327:70-73).

For the purposes of the invention, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822-3828; and McCarty et al. (1991) *J. Virol.* 65:2936-2945. A number of other vectors have been described which encode Rep and/or Cap expression products. See, e.g., U.S. Pat. No. 5,139,941.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97-129; and Kotin, R. M. (1994) *Human Gene Therapy* 5:793-801. Suitable homologues of the AAV rep coding region include the human herpesvirus 6 (HHV-6) rep gene which is also known to mediate AAV-2 DNA replication (Thomson et al. (1994) *Virology* 204:304-311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822-3828; and McCarty et al. (1991) *J. Virol.* 65:2936-2945. A number of other vectors have been described which encode Rep and/or Cap expression products. See, e.g., U.S. Pat. No. 5,139,941.

Both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

AAV Accessory Functions

The host cell (or packaging cell) must also be rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

Particularly, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241-247;

McPherson et al. (1985) *Virology* 147:217-222; Schlehofer et al. (1986) *Virology* 152:110-117.

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon or cosmid. Accessory vectors can also be in the form of one or more linearized DNA or RNA fragments which, when associated with the appropriate control elements and enzymes, can be transcribed or expressed in a host cell to provide accessory functions. See, for example, International Publication No. WO 97/17548, published May 15, 1997.

Nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in *CRC Handbook of Parvoviruses*, vol. I (P. Tijssen, ed.), and Muzyczka, N. (1992) *Curr. Topics. Microbiol. and Immun.* 158:97-129. Specifically, early adenoviral gene regions E1a, E2a, E4, VAI RNA and, possibly, E1b are thought to participate in the accessory process. Janik et al. (1981) *Proc. Natl. Acad. Sci. USA* 78:1925-1929. Herpesvirus-derived accessory functions have been described. See, e.g., Young et al. (1979) *Prog. Med. Virol.* 25:113. Vaccinia virus-derived accessory functions have also been described. See, e.g., Carter, B. J. (1990), supra., Schlehofer et al. (1986) *Virology* 152:110-117.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions are then ready for use for DNA delivery to the CNS (e.g., cranial cavity) of the subject.

Delivery of Viral Vectors

Methods of delivery of viral vectors include, but are not limited to, intra-arterial, intra-muscular, intravenous, intranasal and oral routes. Generally, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

For in vivo delivery, the rAAV virions will be formulated into pharmaceutical compositions and will generally be administered parenterally, e.g., by intramuscular injection directly into skeletal or cardiac muscle or by injection into the CNS.

However, since conventional methods such as injection have not been shown to provide widespread delivery of viral vectors to the brain of the subject, central to the present invention is the discovery that viral vectors are efficiently delivered to the CNS via convection-enhanced delivery (CED) systems. The present inventors are the first to describe and demonstrate that CED can efficiently deliver viral vectors, e.g., AAV, over large regions of an animal's brain (e.g., striatum). As described in detail and exemplified below, these methods are suitable for a variety of viral vectors, for instance AAV vectors carrying reporter genes (e.g., thymidine kinase (tk)) or therapeutic genes (e.g., AADC and tk).

Any convection-enhanced delivery device may be appropriate for delivery of viral vectors. In a preferred embodiment, the device is an osmotic pump or an infusion pump. Both osmotic and infusion pumps are commerically available from a variety of suppliers, for example Alzet Corporation, Hamilton Corporation, Alza, Inc., Palo Alto, Calif.). Typically, a viral vector is delivered via CED devices as follows. A catheter, cannula or other injection device is inserted into CNS tissue in the chosen subject. In view of the teachings herein, one of skill in the art could readily determine which general area of the CNS is an appropriate target. For example, when delivering AAV-AADC to treat PD, the striatum is a suitable area of the brain to target. Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target. Moreover, because the methods described herein can be practiced such that relatively large areas of the brain take up the viral vectors, fewer infusion cannula are needed. Since surgical complications are related to the number of penetrations, the methods described herein also serve to reduce the side effects seen with conventional delivery techniques.

Pharmaceutical compositions will comprise sufficient genetic material to produce a therapeutically effective amount of the protein of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present invention be combined with other suitable compositions and therapies. For instance, as described in detail in the Examples below, Parkinson's disease can be treated by co-administering an AAV vector expressing AADC into the CNS (e.g., into the caudate nucleus or putamen of the striatum) and additional agents, such as dopamine precursors (e.g., L-dopa), inhibitors of dopamine synthesis (e.g., carbidopa), inhibitors of dopamine catabolism (e.g., MaOB inhibitors), dopamine agonists or antagonists can be administered prior or subsequent to or simultaneously with the vector encoding AADC. For example, L-dopa and, optionally, carbidopa, may be administered systemically. In this way, the dopamine which is naturally depleted in PD patients, is restored, apparently by expression of AADC which is able to convert L-dopa into dopamine. Where the transgene (e.g., AADC) is under the control of an inducible promoter, certain systemically-delivered compounds such as muristerone, ponasteron, tetracyline or aufin may be administered in order to regulate expression of the transgene.

Treatment of CNS Disorders

Viral vectors expressing therapeutic transgenes can be used to treat various CNS disorders by providing therapeutic proteins or polypeptides. In a preferred embodiment, the viral vectors are delivered to the CNS via the CED methods described herein as these methods provide the first effective way of broadly distributing viral vectors into the CNS. Non-limiting examples of disorders which may be treated include tumors, injury resulting from stroke and neurodegenerative diseases.

Parkinson's Disease

In a preferred embodiment of the present invention, viral vectors which provide the enzyme AADC are used for the treatment of Parkinson's disease. As described above, Parkinson's disease results from a selective loss of dopaminergic nigrostriatal neurons, resulting in a loss of input from the substantia nigra to the striatum. Animal models of PD have been created, for instance by treating rats or primates with 6-hydroxydopamine (6-OHDA) to destroy dopaminergic cells or by lesioning primates with the neurotoxin 1-methyl-4-phenyl-1,2,3,4-tetrahydropyridine (MPTP), which produces a Parkinson's-like disease.

The present invention provides the first evidence that dopaminergic activity can be restored in Parkinson's patients (e.g., MPTP-lesioned monkeys), by administration of viral vectors carrying the transgene for AADC in combination with systemic (e.g., oral) administration of L-dopa and, optionally, carbidopa. Previous suggestions for gene therapy for Parkinson's have focused on the deficiency of tyrosine hydroxylase as the disease progresses. These suggestions, therefore, call for the restoration of dopamine synthesis in the nigrostriatal pathway by the successful expression of at least three transgenes in order to make dopamine in situ: the tyrosine hydroxylase gene; the gene for the co-factor bioptrene, GTP-cyclohydroxylase-1; and the gene for AADC. In addition to the problems associated with delivering three genes at appropriate levels, the regulation of dopamine levels would be difficult to control using this approach.

The present inventors have demonstrated that one transgene (e.g., AADC) in combination with L-dopa provides therapeutic benefit. AADC is the enzyme involved in the final step of dopamine biosynthesis, converting L-dopa to dopamine. Thus, a clear advantage of the AADC therapeutic approach to restoring dopaminergic activity is that only one gene has to be delivered and the regulation of dopamine levels is possible by controlling peripheral levels of L-dopa. Furthermore, by delivering just the AADC gene, L-dopa can be used as a pro-drug to regulate levels of dopamine in the striatum.

Since AADC-encoding nucleotides delivered by AAV vectors appear to be expressed mainly in the striatal neurons another important therapeutic advantage is the treatment's provision of a buffering mechanism for L-dopa. Many side effects, such as dyskinesisas, are attributed to the inefficient buffering of Parkinsonian brain. The methods described herein avoid this problem by allowing un-metabolized L-dopa to be stored in the neurons. As exemplified below, the delivery of AADC to the MPTP-treated striatum enables conversion of L-dopa to dopamine and the subsequent metabolism to DOPAC and HVA by striatal neurons. Based on FMT PET data, it appears that striatal neurons can also store dopamine, since FMT was visualized in this region. In fact, conversion rates of L-dopa to dopamine following AADC gene transfer were as robust and greater than seen in the normal striatum (see, e.g., FIG. 7). Furthermore, although Parkinson's disease is an progressive disorder, it is not likely that an ongoing degeneration process will affect AADC expression in striatal neurons since they are not typically affected by idopathic Parkinson's disease.

Figure 7:
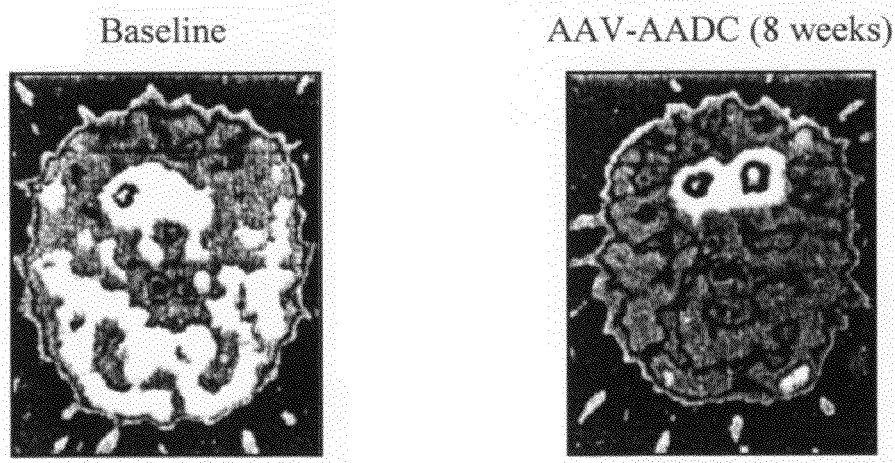
FIG. 7 is an FMT PET scan depicting dopamine activity in the brains of unilaterally MPTP-lesioned monkeys. The left side (baseline) shows limited activity on the lesioned side, while the right side (8 weeks post AAV-AADC administration) shows normal levels of dopamine activity.

The degeneration of the dopaminergic system in patients with idiopathic Parkinson's disease is not uniform. The nigrostriatal pathway degenerates at much faster rate than mesolimbic pathway, leaving patients with an imbalance between the activity of the two pathways. As the disease progresses, higher levels of L-dopa are needed to compensate for the degeneration of the nigrostriatal pathway, but this also results in increasingly higher dopamine levels in the nucleus accumbens and other parts of the mesolimbic system. Such overstimulation may be responsible for some of the side effects associated with L-dopa treatment such as hallucinations. Similarly, MPTP leaves the mesolimbic dopaminergic system relatively spared (see, FIG. 7, no dopaminergic innervation is present in the caudate and putamen, a partial lesion is seen in the nucleus accumbens). As shown in FIG. 7, AAV-AADC can restore this imbalance almost back to normal, therefore, it is possible that lower doses of L-dopa will be required following the restoration of AADC enzyme levels and improved L-dopa to dopamine conversion rates. This in turn might reduce overstimulation of the mesolimbic system, resulting in fewer L-dopa/carbidopa related side effects.

As explained above, the AAV-AADC vectors can be delivered by any suitable method, for example, injection, grafting, infusion, transplantation of cells carrying the vectors, etc. In a preferred embodiment, the vectors are delivered by the CED methods described herein. As exemplified below, such delivery methods provide broad distribution and expression in CNS neurons and thereby provide a novel treatment regime for PD.

Imaging

The present invention also provides methods of determining in vivo activity of an enzyme or other molecule. More specifically, a tracer which specifically tracks the targeted activity is selected and labeled. In a preferred embodiment, the tracer tracks dopamine activity, for example fluoro-L-m-tyrosine (FMT) which binds to cells that utilize dopamine. Suitable labels for the selected tracer include any composition detectable by spectroscopic, photochemical, immunochemical, electrical, optical or chemical means. Useful labels in the present invention include radiolabels (e.g., $^{18}$F, $^{3}$H, $^{125}$I, $^{35}$S, $^{32}$P, etc), enzymes, colorimeteric labels, fluorescent dyes, and the like. In a preferred embodiment, the label $^{18}$F is used with FMT to quantify dopamine activity.

Means of detecting labels are well know to those of skill in the art. For example, radiolabels may be detected using imaging techniques, photographic film or scintillation counters. In a preferred embodiment, the label is detected in vivo in the brain of the subject by imaging techniques, for example positron emission tomography (PET). PET techniques are discussed in detail in Example 3 below.

EXAMPLES

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Construction and Production of AAV-tk

The AAV-tk vector was constructed by placing the herpes simplex virus thymidine kinase (tk) gene under the transcriptional control of the cytomegalovirus (CMV) immediate early promoter in a pUC-based plasmid (available from, Roche Molecular Biochemicals). A β-globin intron was located directly upstream from the tk gene and human growth hormone poly-A was placed downstream. The entire cassette was flanked by AAV inverted terminal repeats (ITRs) that are required for gene expression, replication, and packaging into viral particles.

Recombinant AAV virions were produced in human 293 cells (readily available through, e.g., the American Type Culture Collection under Accession Number ATCC CRL1573) as follows. The 293 cell line was cultured in complete DMEM (Biowhittaker) containing 4.5 g/liter glucose, 10% heat-inactivated fetal calf serum (FCS; Hyclone), and 2 mM glutamine. Subconfluent 293 cells were co-transfected by calcium phosphate precipitation (see, e.g., Sambrook, et al.) with the AAV-tk expression cassette flanked by ITRs and helper plasmids derived froth both AAV (pw1909, containing the AAV rep and cap genes) and adenovirus (pLadenol, containing E2a, E4, and adenoviral $VA_1$ and $VA_{11}$ RNA genes). After 6 hours, the media was changed to DMEM without serum and incubation was continued at 37° C. in 5% $CO_2$ for 72 hours. Pelleted cells were lysed in Tris buffer (100 mM Tris/150 mM NaCl, pH 8-0) by three cycles of freeze/thaw, and lysate was clarified of cell debris by centrifugation at 10,000 g for 15 m. To pellet non-viral proteins, the clarified lysate was centrifuged at 10,000 g for 15 min after adding $CaCl_2$ to a final concentration of 25 mM and incubated for 1 h at 0° C. Polyethylene glycol 8000 (PEG) was added to the resulting supernatant (final concentration=8%); this solution was incubated for 3 h at 0° C. and centrifuged at 3000×g for 30 minutes. The vector-containing pellet was solubilized in 50 mM Hepes Na/150 mM NaCl/25 mM EDTA, pH 8.0, and centrifuged at 10,000×g for 15 minutes to pellet and remove insoluble material.

Cesium chloride isopycnic gradient centrifugation was performed and AAV-tk was recovered from the resulting gradient by isolating the fractions with in average density of 1.38 g/ml. PEG was again used to concentrate vector, which was then resuspended in 25 mM Hepes Na/150 mM NaCl, pH 7.4 and centrifuged as described to remove insoluble material. The stock was treated with DNAse and vector titer was determined by quantitative dot-blot hybridization.

Example 2

In Vivo Delivery of AAV-tk: Dosages and Methods

In order to determine the appropriate dose of AAV to introduce into the brain, the following study was conducted. The striatum was used to test dose response to the AAV vector because of its relatively large area of homogenous tissue and because it is a target for treatment of neurodegenerative disease and other central nervous system disorders.

In addition, efficient methods of delivering vector to the CNS were determined. Simple stereotactic injection of therapeutic agents has been shown to result in limited volume of distribution in brain (Kroll et al, (1996) *Neurosurgery* 38:746-754). Therefore, slow infusion pumps were used to maintain a pressure gradient during intracranial delivery. Previous studies concerned with the delivery of small, medium, and large molecules to brain have demonstrated that slow infusion pump results in extensive and homogenous tissue distribution.

To investigate which method of administering intracranial injection of the vector is most efficient, rats were given 2.5× $10^{10}$ particles of AAV-tk by using the Harvard infusion pump (Harvard Apparatus Inc., Holliston, Mass.) or Alzet subcutaneous osmotic pumps (Alza Scientific Products, Palo Alto, Calif.). Female Sprague-Dawley rats (250-300 g) from Charles River Laboratories (Wilmington, Mass.) were anesthetized with an intraperitoneal injection of ketamine (100 mg/kg body weight) and xylazine (10 mg/kg, body weight) and prepped for surgery. During surgery, sedation was maintained with isofluorane (Attrane, Omeda PPD Inc., Liberty, N.J.) and $O_2$ flow rates were kept at 0.3-0.5 L/m. The head of each rat was fixed in a stereotactic apparatus (Small Animal Stereotactic Frame; ASI Instruments, Warren, Mich.) with ear bars, and a midline incision was made through the skin to expose the cranium. A bore hole was made in the skull 1 mm anterior to the bregma and 2.6 mm lateral to the midline using a small dental drill. Vector was delivered to the left hemisphere and a depth of 5 mm using an infusion pump or subcutaneous osmotic pumps.

For dosage studies, there were 3 groups of animals with 6 animals per group. AAV-tk was continually administered to each rat at a rate of 8 μl/h for 2.5 h using a Harvard infusion pump. The loading chamber (Teflon tubing 1/16th" OD×0.03" ID) and attached infusion chamber (1/16" OD×0.02" ID) were filled with $2.5 \times 10^8$, $2.5 \times 10^9$, or $2.5 \times 10^{10}$ particles of AAV-tk in a total volume of 20 μl artificial csf (148 mM NaCl, 3 mM KCl, 1.4 mM $CaCl_2.2H_2O$, 0-8 mM $MgCl_2.6H_2O$, 1.3 mM $Na_2HPO_4.H_2O$, 0.2 mM $Na_2HPO_4.H_2O$). Delivery was through a 27 gauge needle fitted with fused silica, which was gradually removed 15 m following infusion.

Alternatively, subcutaneous osmotic pumps were used to deliver vector to one group of 6 animals. AAV-tk was continually administered to each rat at a rate of 8 μl/hour for 24 h using Alzet osmotic pumps, model #2001D (ALZA Scientific Products, Palo Alto, Calif.). The pump's reservoir and attached catheter (polyethylene 60 tubing) were filled with $2.5 \times 10^{10}$ particles of AAV-tk in a total volume of 200 μl artificial csf (Harvard Apparatus, Inc., Holliston, Mass.) Delivery was through a 27 gauge cannula fitted with fused silica. After stereotactic placement, the cannula was secured to the skull with a small stainless steel screw and dental cement, and the pump was implanted subcutaneously in the mid-scapular area of the back. The surgical site was closed in anatomical layers with 9 mm wound clips. Twenty four hours later, pumps were removed by clipping and sealing the catheters but the implanted cannulas were left in place. Burr holes were filled with bone wax.

All surgical procedures, animal care and housing, and tissue harvest were performed at the Richmond facility of the Berkeley Antibody Co. (Berkeley, Calif.).

Histology

Animals were euthanized by pentobarbitol overdose (dose) and perfused through the ascending aorta with ice-cold PBS and 4% neutral buffered paraformaldehyde. The brains were removed from the skull, post-fixed by immersion in the same fixative for 24 hr, equilibrated in 30% sucrose, and frozen in −70° C. isopentane. They were then positioned in a cryostat and 40 micron sections were serially collected from the prefrontal cortex to the midbrain. Each brain yielded approximately 150 sections, that spanned an anterior-posterior (AP) length of 6-8 mm. For routine histological analysis, every IP section was stained with H & E. Selected sections representing different brain regions were stained with crystal violet in order to determine general cell density. Results are shown in Table 1.

TABLE 1

|  | Cellular Infilt. Bleeding | Fresh | Hemosiderin | Necrosis Track | Needle |
|---|---|---|---|---|---|
| Infusion Pump ($2 \times 10^8$) | − | − | − | − | Fine lines |
| Infusion Pump ($2 \times 10^9$) | − | − | + | − | Fine lines |
| Infusion Pump ($2 \times 10^{10}$) | − | ++ (1/6) | ++ (4/6) | − | Fine lines |
| Osmotic Pump ($2 \times 10^{10}$) | +++ (5/6) | +++ | ++ | +++ | Holes |

PCR Analysis

Two additional groups of rats, with two animals per group, were treated with $2.5 \times 10^{10}$ particles AAV-tk for the purpose of determining tissue distribution of vector. One of the groups received vector by infusion and the other by osmotic pump, as described above. Animals were euthanized three weeks later using $CO_2$ inhalation and samples from 15 organs and tissues were harvested from each rat including right brain, left brain, spinal cord, right eye, left eye, heart, lung, liver, kidney, spleen, ovary, thymus, lymph node, bone marrow, and leg muscle. Sterile techniques were used and tissue was collected using disposable suture removal kits that were changed between each sample. Tissues were immediately frozen in liquid $N_2$ and kept at −70° C. until they were processed for genomic DNA. PCR was performed using Perkin Elmer's GeneAmp PCR Core Kit and two 30-mer oligos derived from tk sequence (5'-AAGTCATCGGCTCGGGTACGTAGAC-GATATC-3' (SEQ ID NO:1) and 5' ATAGCAGCTACAATC-CAGCTACCATTCTGC-3' (SEQ ID NO:2)). Reactions were performed in a PTC-100 thermal cycler (MJ Reserach, Inc.) and resulted in a 158 bp per product in samples where vector was present.

Immunohistochemisty

Immunocytochemistry was used to detect transgene expression in every section that directly followed one stained with H & E. Thus, one out of every 12 sections was washed in PBS, treated with 3% $H_2O_2$ for 30 m to block endogenous peroxidase activity, rinsed again in $dH_2O$ and PBS, and incubated in blocking solution (10% goat serum+0.01% Triton-X100 in PBS) for 30 m. Next, samples were incubated in polygonal anti-tk antibody (Yale)) (1:1000) for 1 h, washed three times in PBS, incubated in biotinylated goat anti-rabbit IgG (Vector) (1:300) for 1 h, and washed again. Antibody binding was visualized with Streptavidin horseradish peroxidase (1:300) and VIP chromogen (Vector).

Quantitative Analysis

Transgene expression was quantitated for each brain by using a Ken-a-vision microprojector to project tk-immunostained sections onto an ARTZII graphic tablet. The NIH image 1.6 program was used to capture and analyze images. The total estimated number of positive cells for each brain was determined at a magnification of 100× using the following formula:

$$\text{Total tk cell } \# = (n1 + n2 + n3) \times 12 \times k$$

n=positive cells/section k: correction factor derived from the Ambercrombie equation (1946): $k = T/(T+D)$ T=section thickness (40μ), D cell diameter (16μ); k=0.71

The volumes of the tk-immunoreactive regions were determined by measuring areas of tk expression using captured images projected at 50× magnification and calculating as follows:

$$V = A_x \times L$$
$$A_x = \text{average area (mm}^2\text{)} = \frac{a1 + a2 + a3 \ldots An}{n}$$

(where, L=AP distance (μ) of staining=n×12×40 u and n=# of stained sections)

To determine how much virus is required to efficiently transduce brain tissue, comparisons of immunostained sections were performed between rats receiving $2.5 \times 10^8$, $2.5 \times 10^9$, or $2.5 \times 10^{10}$ particles of AAV-tk via the Harvard infusion pump.

Figure 1B:
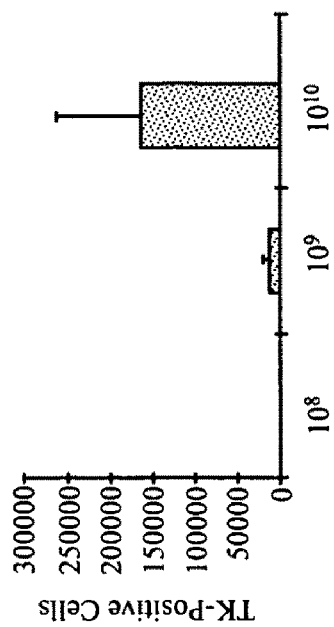
Figure 1C:
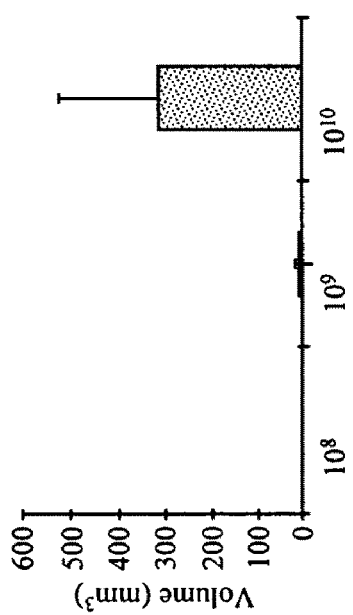
Figure 1D:
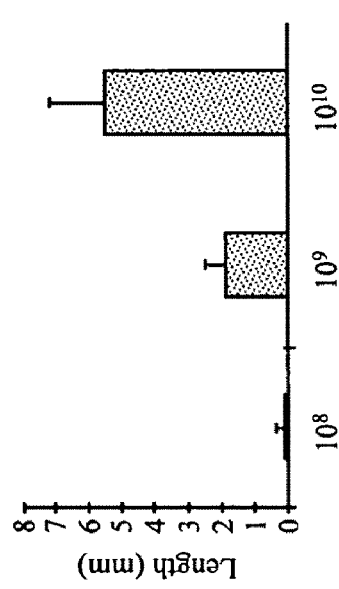
Figure 2:
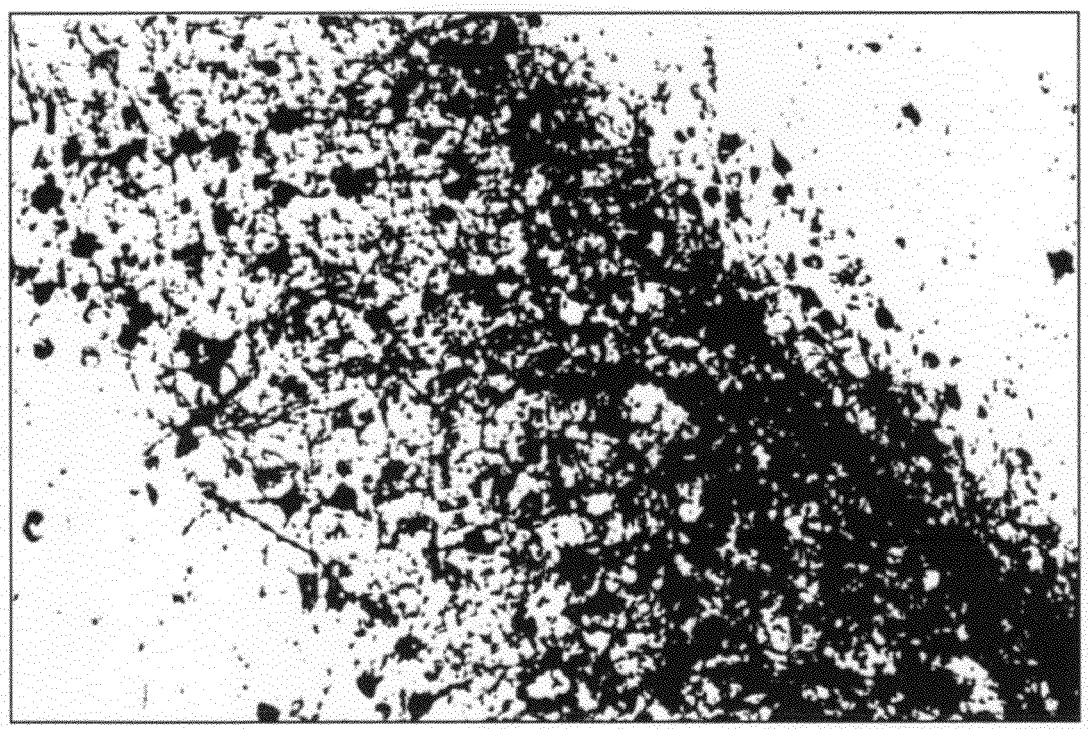
FIG. 2 is a half-tone reproduction showing labeling of rat brain tissue after injection of AAV vectors.
Figure 3B:
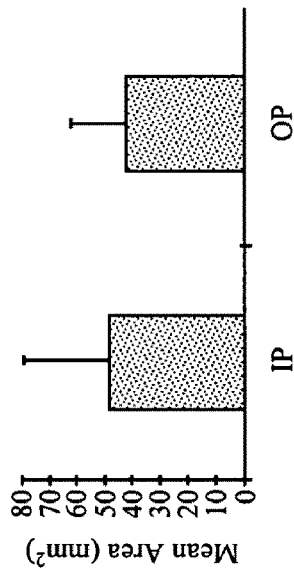
FIG. 3, panels a though d, depict intracranial delivery of AAV-tk through either an infusion pump (IP) or osmotic pump (OP). The tissue volume (FIG. 3a); mean area (FIG. 3b); length (FIG. 3c) and number of cells (FIG. 3d) expressing the transgene are depicted.
Figure 3D:
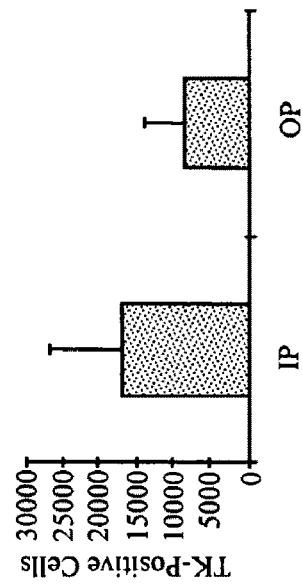
Figure 3A:
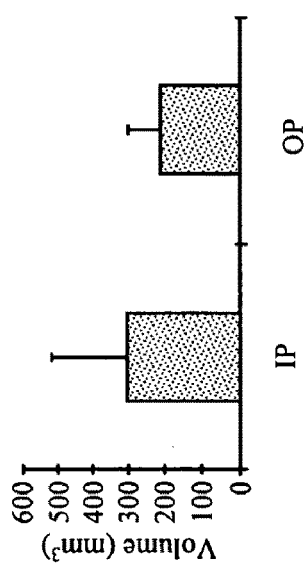
Figure 3C:
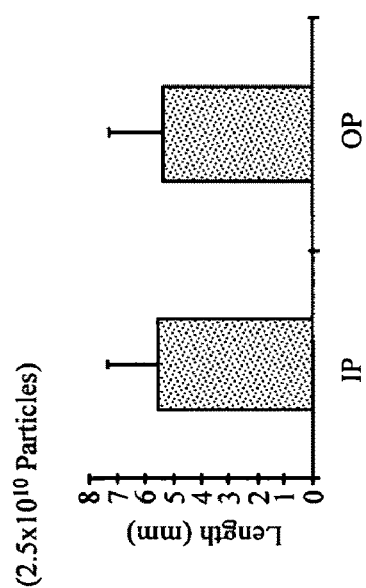

With all parameters measured, a clear dose response was observed. Infused tissue from animals receiving the highest titer demonstrated transgene expression in an average of 300 mm³ of tissue (or approximately 60% of an adult rat cerebral hemisphere (Leyden et al. (1998) *Behav. Brain Res.* 87:59-67) as compared to volumes of 10 mm³ for the middle-dose group and <1 mm³ for the low-dose group (FIG. 1a). Volumes were calculated from the mean areas and lengths of staining which both also showed significant differences between the groups (FIG. 1b,c). Expression within a volume of transduced tissue was not uniform, however, but exhibited a gradient of staining. Areas directly surrounding the injection sites were heavily labeled while fewer positive cells could be detected as distance from the needle tract increased (FIG. 2). Finally, FIG. 1d illustrates that the total number of tk-positive cells in section, from the high dose group, estimated to average 169,000, is approximately 10× higher than that of the middle dose group.

Infusion Versus Osmotic Pump Delivery

Figure 4A:
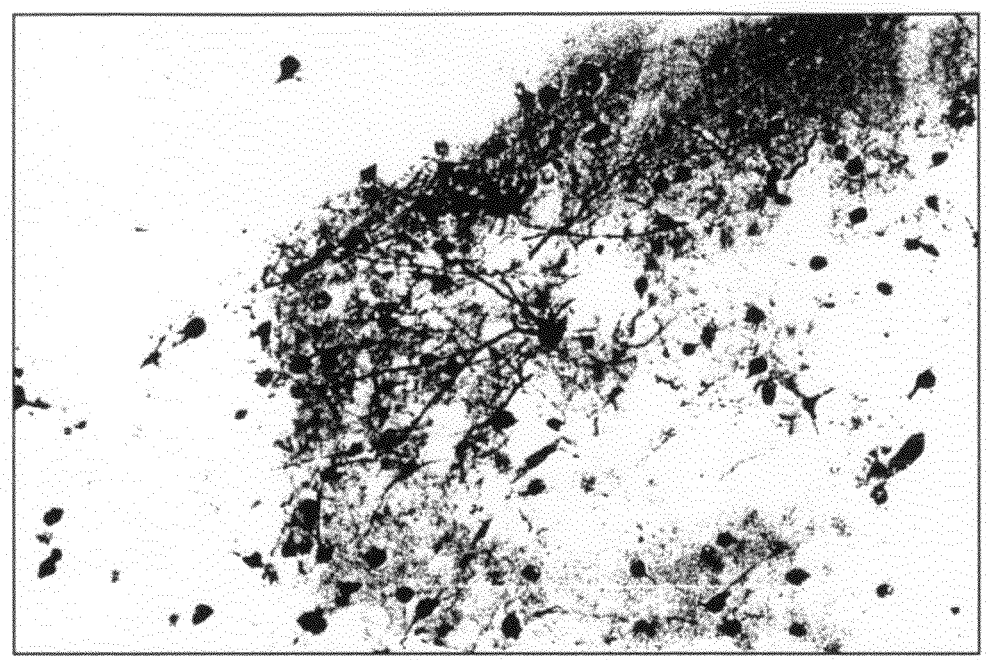
FIGS. 4a, 4b, 4c and 4d are half-tone reproductions depicting CNS tissue infused with vector carrying the tk transgene.
Figure 4B:
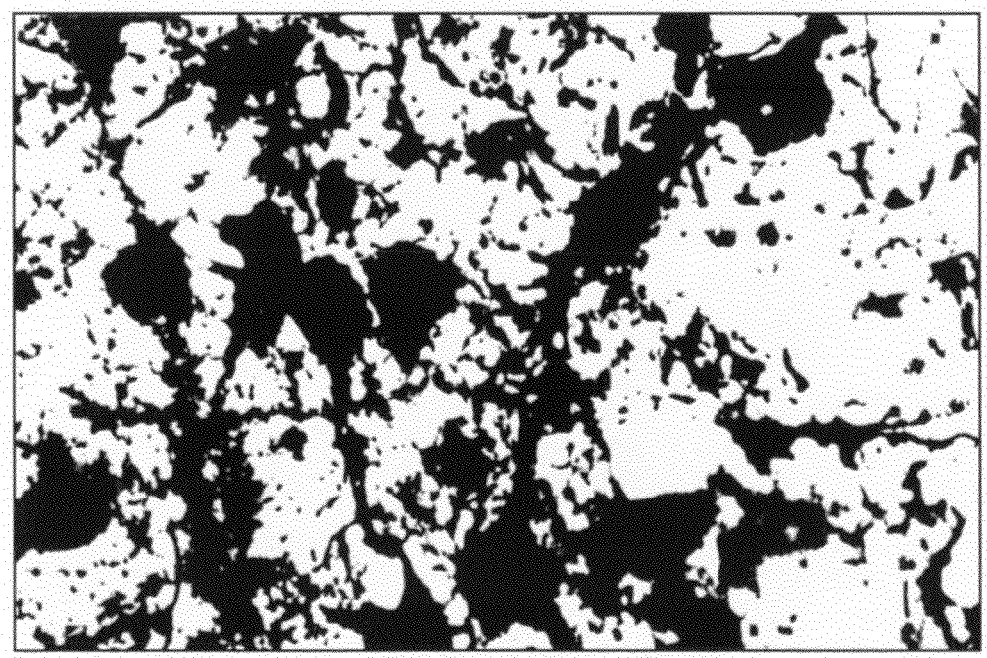
Figure 4C:
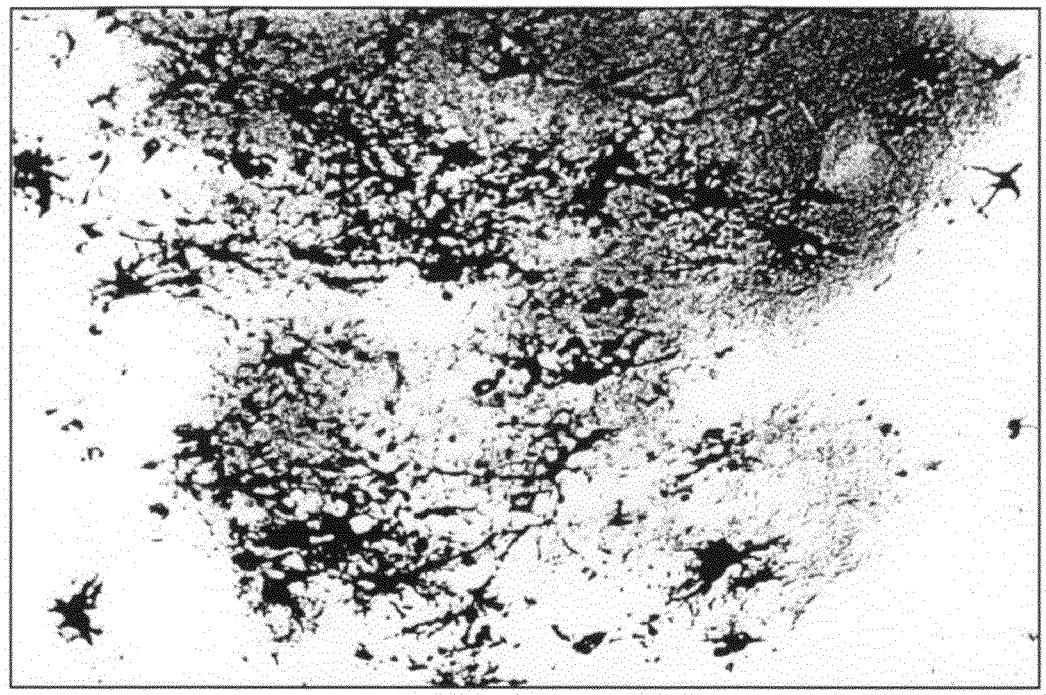
Figure 4D:
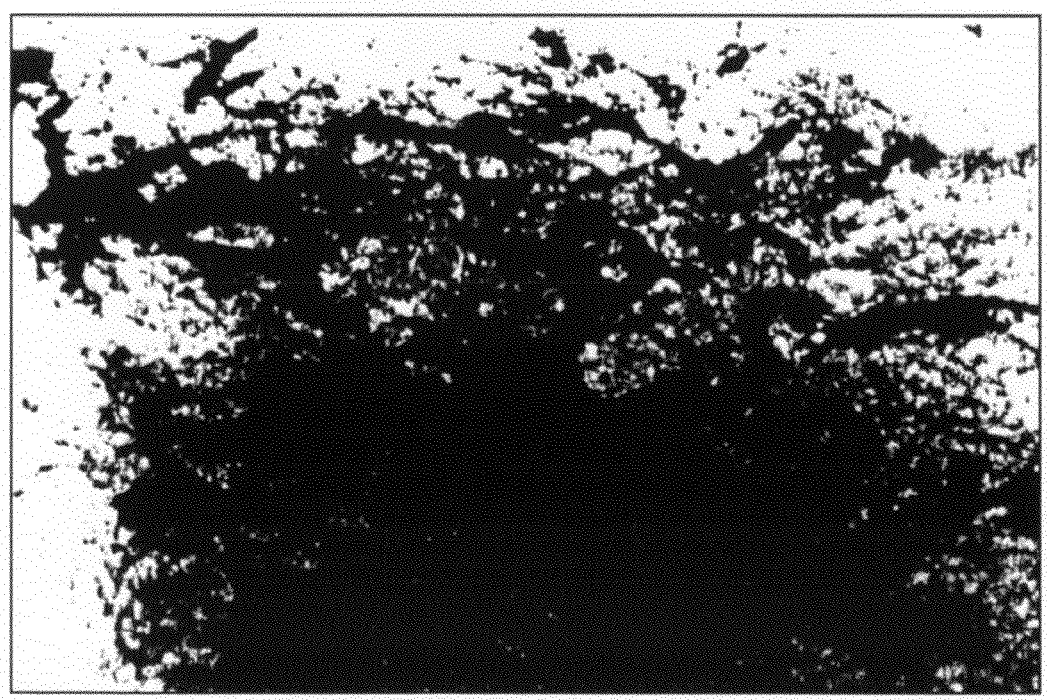
Figure 5:
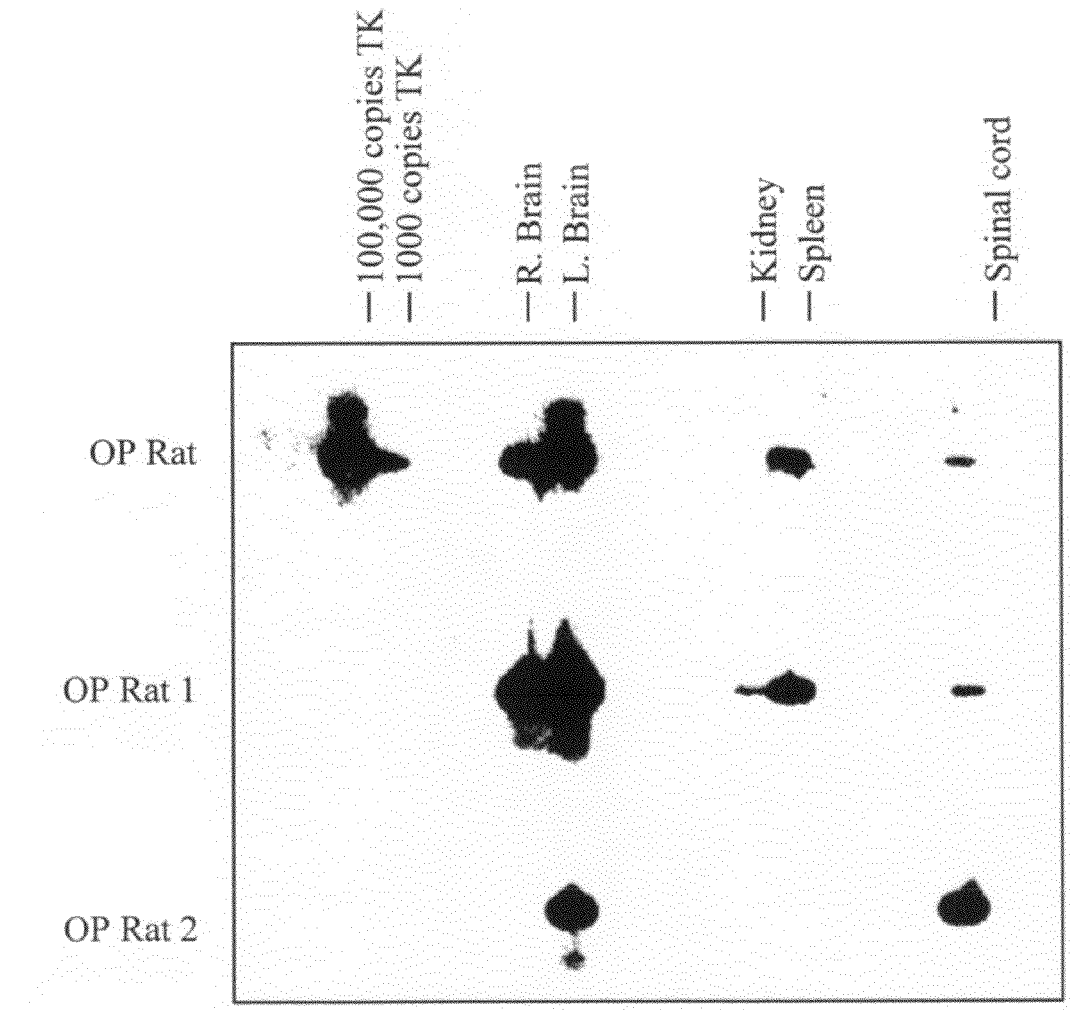
FIG. 5 is a half-tone reproduction depicting Southern blot analysis of tissues from a subject infused with AAV-tk vector.

Comparisons of immunostained brain sections demonstrated similarities and differences in the abilities of the two pumps to deliver vector. There was no significant difference in tk expression between the two groups as measured by mean volume, area, AP distance, and total estimated number of positive cells (FIG. 3a-d). Because there was some tissue loss surrounding the needle tracts of all of the samples within the osmotic pump delivery group (data not shown), that group's true mean value for the number of estimated positive cells may be higher. And, while both delivery methods resulted in notable transgene expression, there was a difference in the type of cells that became labeled. Tissue infused with vector expressed tk almost exclusively in neurons (FIG. 4a,b) and tissue receiving vector via osmotic pump exhibited expression in neurons and in reactive glial cells close to the site of injection (FIG. 4c,d).

Tissue Distribution

Figure 6:
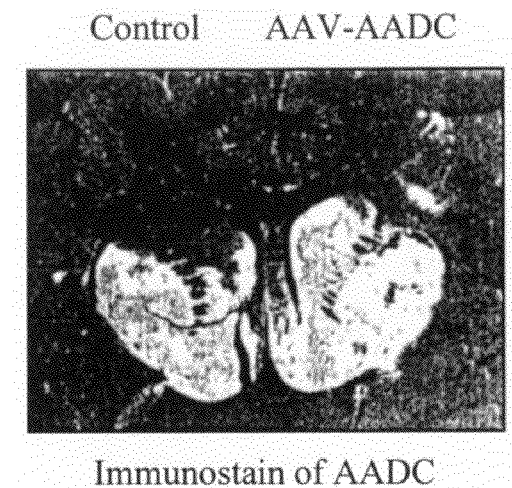
FIG. 6 depicts immunostaining for AADC of the brains of MPTP-lesioned monkeys. The left side (control) shows limited staining, while the right side (AAV-AADC treated) shows broad AADC immunostaining.

To determine if recombinant AAV could be detected at locations distant from the site of intracranial delivery, PCR analysis was performed on 15 different organs and tissue from each of three rats who had received a high dose of vector. Regardless of the delivery method (infusion or osmotic pumps), a 458 bp PCR product from the tk gene could be detected in spinal cord, spleen, and both hemispheres of the brain using Southern blot analysis (FIG. 6). In one of the rats, vector sets were also detected in tissue from the kidney.

Toxicity

To assess whether or not toxicity was associated with any of the delivery methods, histopathology was performed on H & E sections from each group and the results are summarized in table 1. Overall tissue morphology was well preserved and no freezing or other artifacts were present. In the infusion delivery groups, tissue damage was minimal, if present at all. There was no cellular infiltration, no necrosis in the needle tract, and minimal cortical necrosis in a few of the animals. Fresh bleeding was found in one of the high-dose rats, and hemosiderosis, indicating moderate bleeding in the past, was found in four of the high-dose animals. Alternatively, serious damage was noted in all of the animals in the osmotic pump delivery group including large necrotic areas surrounding the needle tract, cellular infiltrates, and hemosiderosis.

Thus, infusion of $2.5 \times 10^{10}$ particles of AAV-tk at 8 μl/h for 2.5 h is sufficient to partially distribute AAV vector to a volume of 300 mm³ of tissue. Within this region, a gradient of expression is observed with heavy staining directly surrounding the site of injection and fewer positive cells farther away. Distribution appears to be a function of dose (particle number) and not a function of delivery time or sample volume when two different pump delivery systems are compared: the distribution of $2.5 \times 10^{10}$ particles was the same whether it was delivered by osmotic pump (volume=200 μl, rate=8 μl/h, time=24 h) or infusion pump (volume=20 μl, rate=8 μl/h, time=2.5 h). Furthermore, strikingly different levels of expression were observed between the three infusion delivery groups, where sample volume, rate, and delivery time were kept constant and particle number was the only variable.

These results obtained with convection-enhanced delivery of AAV are consistent with those obtained from CED studies of large macromolecules, such as supramagnetic particles to rat brains. (Kroll et al. (1996) *Neurosurg.* 38:746-754, U.S. Pat. No. 5,720,720). Kroll et al. used magnetic resonance imaging and histochemical staining demonstrated that dose was the most important variable in maximizing the distribution of particles in tissue. Kroll reports that regardless of whether the infusion volume was small (2 μl) or moderate (24 μl) or whether the infusion rate was low (60 μl/h) or high (72 μl/h), increasing the particles from 5.3 to 26.5 μg resulted in as much as a 5-fold increase in the volume of their distribution in tissue.

Concerning cell-type specificity, it has been previously reported that AAV is capable of transducing neurons and the present study confirms this finding. The fact that expression was so prominent in neurons suggests that AAV gene therapy vectors employing the CMV promoter are useful for treatment of neurodegenerative diseases such as Parkinson's and Alzheimer's disease. No expression was seen in mature glial cells, except in small areas of disturbed tissue where active gliosis was present. However, we have previously demonstrated that the AAV-CMV-tk vector is expressed well in glioma cells and, when given in conjunction with the prodrug ganciclovir, is effective in treating experimental gliomas in nude mice. Because the tk "suicide" gene is thought to be toxic to dividing cells, it should pose a risk only to the targeted tumor cells and not to surrounding neurons. Finally, while the CMV promoter used in this study allows for strong transgene expression in neurons, the choice of cell-type-specific promoters will allow targeting of AAV to other CNS components such as oligodendrocytes and glial calls.

The present study also shows that AAV delivered to brain is contained mostly in the central nervous system. Others have demonstrated retrograde transport of viruses between the two hemispheres of brain and ability of viruses to reach spinal cord via circulating cerebral spinal fluid. The appearance of vector in the spleen is curious, and suggests a couple of mechanisms. One is that virus enters the bloodstream during the infusion process and circulated through the spleen where it is "scavenged". If this were the case, however, other tissues that have been shown to be inducible by AAV would be expected to also take up virus. Another possible mechanism could be one exhibited by dendritic cells. These cells found mostly in skin, take up foreign material, enter the circulation, and concentrate in the spleen where the foreign matter can exist for long periods of time awaiting further processing or destruction. In any case, we have found that regardless of the route of delivery, including intramuscular, intravenous, and now intracerebral, vector is always detected in the spleen.

In summary, slow intracranial infusion of high doses of AAV vector has been shown to transduce a significant portion or brain in a rodent model. AAV may be used to target a myriad of central nervous disorders, including tumors, injury resulting from stroke, and neurodegenerative disease.

Example 3

Gene Therapy of Parkinson's Disease

Convection-enhanced delivery of AAV vectors carrying the transgene encoding AADC was shown to restore dopaminergic systems in MPTP-induced Parkinson's disease in monkeys as follows.

Animals

Rhesus monkeys (n=4, 3-5 kg) were chosen as candidates for implantation based on the evolution of their parkinsonian symptoms. Animals were lesioned by infusing 2.5-3.5 mg of MPTP-HLC through the right internal carotid artery (referred to as ipsilateral side) followed by 4 I.V. doses of 0.3 mg/kg of MPTP-HCL (referred to as contralateral side) until a stable, overlesioned hemi-parkinsonian syndrome was achieved (Eberling, (1998) *Brain Res.* 805:259-262). The primate MPTP model is considered the gold standard model of evaluation prior to human trials. (Langston (1985) *Trends Pharmcol. Sci.* 6:375-378). MPTP is it converted in the CNS to MPP+ by monoamine oxidase B. MPP+ is a potent neurotoxin which causes degeneration of the nigral dopaminergic neurons and loss of the nigro-striatal dopamine pathway, as seen in Parkinson's disease. MPTP-lesioned animals were clinically evaluated once a week using a clinical rating scale and activity monitoring for 5 months prior to surgery.

Following MPTP administration, the animals developed clinical signs of Parkinson's disease manifested by general slowness, bradykinesia, rigidity, balance disturbances, and flexed posture. The left arm was less frequently used than the right in all of the monkeys, and all showed signs of tremor. Using the clinical rating scale, all of the monkeys had moderate to severe stable parkinsonian scores (23±1.7, 23±1.2, 24±1.7, 19±3) during the 5 month post-MPTP period.

Vector Production 1. pAAV-AADC:

A 1.5 kb BamHI/PvuII human AADC cDNA (Fan et al. (1998) *Human Gene Therapy* 9:2527-2535) was cloned into the AAV expression cassette pV4.1c at BamHI/HindII sites. The expression cassette contains a CMV promoter, a chimeric intron composed of a CMV splice donor and a human β-globin splice acceptor site, human growth hormone polyadenylation sequence, and flanking AAV ITRs (inverted terminal repeats) (Herzog, R. W., et al. (1999) *Nature Medicine* 5:56-63.).

2. pAAV-LacZ:

The vector pAAV-LacZ was constructed as follows. The AAV coding region of pSub201 (Samulski et al. (1987) *J. Virol* 61:3096-3101), between the XbaI sites, was replaced with EcoRI linkers, resulting in plasmid pAS203. The EcoRI to HindIII fragment of pCMVβ (CLONETECH) was rendered blunt ended and cloned in the Klenow treated EcoRI site of pAS203 to yield pAAV-lacZ.

3. pHLp19:

Plasmid H19 encodes a modified AAV-2 genome designed to enhanced AAV vector production while suppressing the generation of replication competent pseudo-wild type virus. The plasmid contains a P5 promoter moved to a position 3' of the cap gene and the promoter is replaced by a 5' untranslated region primarily composed of a FLP recombinase recognition sequence. pH19 was constructed so as to eliminate any regions of homology between the 3' and 5' ends of the AAV genome. Additionally, the seven base pair TATA box of the pH19 P5 promoter was destroyed by mutation of that sequence to GGGGGGG.

pH19 was constructed, in a several step process using AAV-2 sequences derived from the AAV-2 provirus, pSM620. pSM620 was digested with SmaI and PvuII, and the 4543 bp, rep and cap gene encoding SmaI fragment was cloned into the SmaI site of pUC119 to produce the 7705 bp plasmid, pUCrepcap. The remaining ITR sequences flanking the rep and cap genes were then deleted by oligonucleotide-directed mutagenesis using the following oligonucleotides:

```
                                          (SEQ ID NO: 3)
145A; 5'-GCT CGG TAC CCG GGC GGA
       GGG GTG GAG TCG-3'

(SEQ ID NO: 4)
145B; 5'-TAA TCA TTA ACT ACA GCC
       CGG GGA TCC TCT-3'
```

The resulting plasmid, pUCRepCapMutated (pUCRCM) (7559 bp) contains the entire AAV-2 genome without any ITR sequence (4389 bp). SrfI sites, in part introduced by the mutagenic oligonucleotides, flank the rep and cap genes in this construct. The AAV sequences correspond to AAV-2 positions 146-4,534.

An Eco47III site was introduced at the 3' end of the P5 promoter in order to facilitate excision of the P5 promoter sequences. To do this, pUCRCM was mutagenized with primer P547 (5'-GGT TTG AAC GAG CGC TCG CCA TGC-3') (SEQ ID NO:5). The resulting 7559 bp plasmid was called pUCRCM47III.

The polylinker of pBSIIsk+ was changed by excision of the original with BSSHII and replacement with oligonucleotides blunt 1 and 2. The resulting plasmid, bluntscript, is 2830 bp in length and the new polylinker encodes the restriction sites EcoRV, HpaI, SrfI, PmeI, and Eco47III. The blunt 1 and 2 sequences are as follows:

```
                                          (SEQ ID NO: 6)
blunt 1; 5'-CGC GCC GAT ATC GTT AAC GCC
         CGG GCG TTT AAA CAG CGC TGG-3'

(SEQ ID NO: 7)
blunt 2; 5'-CGC GCC AGC GCT GTT TAA ACG
         CCC GGG CGT TAA CGA TAT CGG-3'
``` pH1 was constructed by ligating the 4398 bp, rep and cap gene encoding SmaI fragment from pUCRCM into the SmaI site of pBluntscript such that the HpaI site was proximal to the rep gene. pH1 is 7228 bp in length.

pH2 is identical to pH1 except that the P5 promoter of pH1 is replaced by the 5' untranslated region of pGN1909. To do this, the 329 bp AscI(blunt)-SfiI fragment encoding the 5' untranslated region from pW1909lacZ was ligated into the 6831 bp SmaI(partial)-SfiI fragment of pH1 creating pH2. pH2 is 7156 bp in length.

A P5 promoter was added to the 3' end of pH2 by insertion of the 172 bp, SmaI-Eco43 µl fragment encoding the p5 promoter from pUCRCM47III into the Eco47III site in pH2. This fragment was oriented such that the direction of transcription of all three AAV promoters are the same. This construct is 7327 bp in length.

The TATA box of the 3' P5 (AAV-2 positions 255-261, sequence TATTTAA) was eliminated by changing the sequence to GGGGGGG using the mutagenic oligonucleotide 5DIVE2 (5'-TGT GGT CAC GCT GGG GGG GGG GGC CCG AGT GAG CAC G-3') (SEQ ID NO: 8). The resulting construct, pH19, is 7328 bp in length.

4. Pladeno5:

Pladeno 5 is a plasmid that provides a complete set of adenovirus helper functions for AAV vector production when transfected into 293 cells. Essentially, it is composed of the E2A, E4, and VA RNA regions from adenovirus-2 and a plasmid back bone. The plasmid was constructed as follows.

pBSIIs/k+ was modified to replace the 637 bp region encoding the polylinker and alpha complementation cassette with a single EcoRV site using oligonucleotide directed mutagenesis and the following oligonucleotide: 5'-CCG CTA CAG GGC GCG ATA TCA GCT CAC TCA A-3' (SEQ ID NO:9). A polylinker encoding the restriction sites BamHI, KpnI, SrfI, XbaI, ClaI, Bst1107I, SalI, PmeI, and NdeI was then cloned into the EcoRV site (5'-GGA TCC GGT ACC GCC CGG GCT CTA GAA TCG ATG TAT ACG TCG ACG TTT AAA CCA TAT G-3') (SEQ ID NO:10).

Adenovirus-2 DNA was digested and restriction fragments encoding the E2A region (a 5,335 bp, KpnI-SrfI fragment corresponding to positions 22,233-27,568 of the adenovirus-2 genome) and the VA RNAs (a 731 bp, EcoRV-SacII fragment corresponding to positions 10,426-11,157 of the adenovirus-2 genome) were isolated. The E2A fragment was installed between the SalI and KpnI sites of the polylinker. An E4 region was first assembled in pBSIIs/k+ by ligating a 13,864 bp, BamHI-AvrII fragment corresponding to adenovirus-2 positions 21,606-35,470 (encoding the 5' end of the gene) and a 462 bp, AvrII and SrfI, digested PCR fragment corresponding to adenovirus-2 positions 35,371-35,833 (encoding the 3' end of the gene) between the BamHI and SmaI sites of pBSIIs/k+. The oligonucleotides used to produce the PCR fragment were designed to introduce a SrfI site at the junction were the E4 promoter and the adenovirus terminal repeat intersect and have the sequences 5'-AGA GGC CCG GGC GTT TTA GGG CGG AGT AAC TTG C-3' (SEQ ID NO:11) and 5'-ACA TAC CCG CAG GCG TAG AGA C-3' (SEQ ID NO:12). The intact E4 region was excised by cleavage with SrfI and SpeI and the 3,189 bp fragment corresponding to adenovirus-2 positions 32,644-35,833 was cloned into the E2A intermediate between the SrfI and XbaI sites. Finally, the VA RNA fragment was inserted into the Bst1107 site after T4 polymerase-mediated blunt end modification of the SacII site. The genes in pladeno 5 are arranged such that the 5' ends of the E2A and E4 promoters abut, causing the regions to transcribe away from each other in opposite directions. The VA RNA genes, which are located at the three prime end of the E4 gene, transcribe towards the E4 gene. The plasmid is 11,619 bp in length.

AAV Vector Production

The HEK 293 cell line (Graham, F. L., Smiley, J., Russel, W. C., and Naiva, R. (1977) Characteristics of a human cell line transformed by DNA from human adenovirus type 5. *J. Gen. Virol.* 36:59-72.) was cultured in complete DMEM (Bio-Whittaker) containing 4.5 gaiter glucose, 10% heat-inactivated fetal calf serum (FCS), and 2 mM glutamine at 37° C. in 5% $CO_2$ in air. Forty T225 flasks were seeded with $2.5 \times 10^6$ cells each and grown for three days prior to transfection to 70-80% confluency (approximately $1.5 \times 10^7$ cells per flask).

The transfection and purification methods described by Matsushita et al (Matsushita, T., Elliger, S., Elliger, C., Podsakoff, G., Villarreal, L., Kurtzman, G. J., Iwaki, Y., and Colosi, P. (1998) "Adeno-associated virus vectors can be efficiently produced without helper virus,"*Gene Therapy* 5:938-945) were employed for AAV vector production, with minor modifications. The vector production process involved co-transfection of HEK 293 cells with 20 µg of each of the following three plasmids per flask: the AAV-AADC plasmid, the AAV helper plasmid (pHLP19, containing the AAV rep and cap genes), and the adenovirus helper plasmid (pladeno-5, previously known as pVAE2AE4-2 (4) and composed of the E2A, E4, and VA RNA genes derived from purified adenovirus-2), using the calcium phosphate method (Wigler, M. et al. (1980) Transformation of mammalian cells with an amplifiable dominant-acting gene. *Proc. Natl. Acad. Sci. USA* 77:3567-3570) for a period of 6 hrs. After transfection, the media was replaced and the cells were harvested 3 days later. The cell pellets were then subjected to 3 cycles of freeze-thaw lysis (alternating between dry ice-ethanol and 37° C. baths with intermittent vortexing). The cell debris was removed by centrifugation (10,000 g for 15 min). The supernatant was centrifuged a second time to remove any remaining turbidity and subsequently treated with Benzonase® (200 u/ml) at 37° C. for 1 hr in order to reduce contaminating cellular DNA. Following incubation, the supernatant was made 25 mM in $CaCl_2$, and was placed on ice for 1 hr. The resulting precipitate was removed by centrifugation (10,000 g for 15 min.) and discarded. The supernatant was then made 10% in PEG (8000), and was placed on ice for 3 hrs. The precipitate was collected by centrifugation (3000 g for 30 min) and resuspended in 4 ml of 50 mM NaHEPES, 0.15M NaCl, 25 mM EDTA (pH 8.0) per 20 T225 flasks. Solid CsCl was added to produce a density of 1.4 g/ml and the sample was centrifuged at 150,000 g for 24 hrs in a Beckman TI70 rotor. AAV-containing fractions were pooled, adjusted to a density of 1.4 g/ml CsCl, and centrifuged at 350,000 g for 16 hrs in a Beckman NVT65 rotor. The fractions containing AAV were then concentrated and diafiltered against excipient buffer (5% sorbitol in PBS). The titer of the purified AAV-AADC vector was determined using quantitative dot blot analysis and vector stocks were stored at ±80° C.

Viral Infusion

In the surgery room, a sterile field was created to prepare the infusion system. Infusion cannulae were flushed with saline to assess the integrity between the needle and tubing interface. Sterile infusion cannulae and loading lines were connected using the appropriate fittings with extreme caution taken to prevent the collection of air bubbles in the system. Non-sterile oil infusion lines were prepared as previously described and 1 ml gas tight Hamilton syringes filled with oil were attached to a Harvard infusion pump. Six infusion cannulae were fitted onto microdialysis holders (3 cannulae per holder) and mounted onto a stereotactic tower. Following the union of the oil and loading lines, the needle cannulae were primed with AAV and the infusion system transferred to the surgery table. Initial infusion rates were set at 0.1 pl/min., the lines visually inspected to ensure a smooth flow of fluid through the system, and the cannulae manually lowered to their target sites. A final visual inspection was performed to check for any air bubbles in the infusion system.

The cannula system consisted of three components: (i) a sterile infusion cannula; (ii) a sterile loading line housing AAV-AADC or AAV-LacZ (control); and (iii) a non-sterile infusion line containing olive oil. Preparation of each line is described here briefly. The infusion cannula consisted of 27 G needles (outer diameter, 0.03"; inner diameter, 0.06"; Terumo Corp., Elkton, Md.) fitted with fused silica (outer diameter, 0.016", inner diameter, 0.008"; Polymicro Technologies, Phoenix, Ariz.), and placed in Teflon tubing (0.03" ID, Upchurch Scientific, Seattle, Wash.) such that the distal tip of the silica extended approximately 15 mm out of the tubing. The needle was secured into the tubing using superglue and the system was checked for leaks prior to use. At the proximal end of the tubing, a Tefzel fitting and ferrule were attached to connect the adjacent loading line.

Loading and infusion lines consisted of 50 cm sections of Teflon tubing (outer diameter, 0.062"; inner diameter, 0.03") fitted with Tefzel 1/16" ferrules, unions, and male Luer-lock adapters (Upchurch Scientific, Oak Harbor, Wash.) at the distal ends. The sterile loading lines accommodated up to a 1000 ml volume and were primed with saline prior to use.

The animals were initially sedated with Ketamine (Ketaset; 10 mg/kg, i.m.), intubated and prepped for surgery. A venous line was established using a 22 gauge catheter positioned in the cephalic or saphenous vein to deliver isotonic fluids at 5-10 ml/kg/hr. Isoflurane (Aerrane, Omeda PPD Inc., Liberty, N.J.) was delivered at 1-3% until the animal maintained a stable plane of anesthesia. The head was placed in an MRI compatible stereotactic frame according to pre-set values attained during a baseline MRI scan. The animal was instrumented with subcutaneous electrocardiogram electrodes, a rectal probe and the body covered with circulating water blankets to maintain a core temperature of 36-38° C. Electrocardiogram and heart rate (using the Silogic ECG-60, Stewartstown, Pa.) and body temperature were continuously monitored during the procedure. The head was prepped with Betadine and 70% ethanol, a sterile field was created and a midline incision performed through the skin, muscle and fascia using electrocautery (Surgistat Electrosurgery, Valleylab Inc., Boulder, Colo.).

Gentle retraction of fascia and muscle allowed for cranial exposure over cortical entry sites. A unilateral craniotomy was performed using a Dremel dental drill to expose a 3 cm×2 cm area of dura mater above the target sites. Multiple needle cannulae attached to a holder were stereotactically guided to striatal target sites. Surgical parameters for unilateral infusion of AAV into the hemisphere ipsilateral to ICA MPTP infusion are summarized in Table 2.

TABLE 2

Surgical Parameters for AAV infusion

| | |
|---|---|
| Target Sites | Striatum (2 caudate, 4 putamen) |
| Hemisphere | right side (ipsilateral to ICA MPTP infusion) |
| Infusion Volume | 30 µl/site |
| Infusion Rates | 0.1 µl/min (60 min) |
| | 0.2 µl/min (60 min) |
| | 0.4 µl/min (30 min) |
| Virus | AAV-AADC; 2.1 × 10e12 particles/ml; Lot no 176.12; 200 µl/vial |
| Control Article | AAV-LacZ; 9.2 × 10e11 particles/ml; Lot no. 176.126; 200 µl/vial |

Approximately fifteen minutes following infusion, the cannulae assembly was raised at a rate of 1 mm/min. until it was out of the cortex. The cortex was rinsed with saline, the bone margins trimmed with ronguers and the wound site closed in anatomical layers. Analgesics (Numorphan, 1M) and antibiotics (Flocillin, 1M) were administered as part of the surgical protocol. Animals were monitored for full recovery from anesthesia, placed in their home cages and clinically observed (2×/day) for approximately five days following surgery. Total neurosurgery time was 4.5 hours per animal.

Following intrastriatal AAV administration, animals were assessed for any signs of abnormal behavior. Animals were observed and rated by the veterinary technicians twice a day using clinical observation forms. All monkeys recovered from the surgery within 2 hours and were able to maintain themselves, including feeding and grooming. There were no signs of any adverse effects during the entire 8-week post-surgical period.

Magnetic Resonance Imaging

Visualization of the target site is crucial for the precise placement of cells within the caudate nucleus or putamen. Stereotactic procedures combined with MRI were used in order to accurately place the cannula within the desired targeted structures. All animals were scanned before surgery to generate accurate stereotactic coordinates of the target implant sites for each individual animal. The same fiducial markers that are used for PET scanning were placed on the frame for co-registration of MRI and PET images. Briefly, during the scanning procedure, the animals were sedated using a mixture of ketamine (Ketaset, 7 mg/kg, im) and xylazine (Rompun, 3 mg/kg, im). The animals were placed in an MRI compatible stereotactic frame, earbar and eyebar measurements were recorded, and an IV line was established. Sixty coronal images (1 mm) and 15 sagittal images (3 mm) were taken using a GE Signa 1.5 Tesla machine. Magnetic resonance images were T1-weighted and obtained in three planes using a spoil grass sequence with a repetition time (TR)=700 ms, an echo time (TE)=20 ms and a flip angle of 30'). The field of view was 15 cm, with a 192 matrix and a 2 NEX (number of averages per signal information). Baseline scanning time was approximately 20 minutes. Rostro-caudal and medio-lateral distribution of a targeted structure (e.g., caudate nucleus) was determined using the coronal MR images. Surgical coordinates were determined from magnified coronal images (1.5×) of the caudate nucleus and putamen.

Positron Emission Tomography (PET)

All 4 animals received 2 PET scans, a baseline scan following establishment of the MPTP lesion, and a second scan 7-8 weeks after infusion with either AAV-AADC or AAV-LacZ. Prior to PET, each animal underwent magnetic resonance (MR) imaging using a 1.5 T magnet and a stereotaxic frame which permitted coregistration between PET and MR data sets through the use of external fiducial markers. The PET studies were performed on the PET-600 system, a single-slice tomograph with a resolution of 2.6 mm in-plane and an adjustable axial resolution which was increased from 6 mm to 3 mm for the current study by decreasing the shielding gap. The characteristics of this tomograph have been described previously (Budinger et al. (1991) *Nucl. Med. Biol.* 23(6): 659-667; Valk, (1990) *Radiology* 176(3):783-790). The monkeys were intubated and anesthetized with isoflurane, placed in a stereotaxic frame and positioned in the PET scanner so as to image a coronal brain slice passing through the striatum. Monkeys were positioned in the same way for each study using the anterior-posterior scales on the sterotaxic frame and a laser light connected to the tomograph. After being positioned in the scanner, a 5 min transmission scan was obtained in order to correct for photon attenuation, and to check the positioning of the animal. The monkeys were then injected with 10-15 mCi of the AADC tracer, 6-[$^{18}$F]fluoro-L-m-tyrosine (FMT) and imaging began. Imaging continued for 60 min, at which time the monkey was repositioned so as to image a second slice 6 mm caudal to the first.

The PET and MR datasets were co-registered and regions of interest (ROs) were drawn for the striatum in the contralateral hemisphere (the side opposite to ICA MPTP infusion) on PET data collected at 50 to 60 min (slice 1) and from 65 to 75 min (slice 2) with reference to the MR. Mirror images of the ROs were created in the ipsilateral hemisphere (side of MPTP infusion) and radioactivity counts ($cm^2$/sec) were determined for each ROI. Striatal counts were averaged over the two slices for each study. FMT uptake asymmetry ratios were calculated for each animal at each time point by subtracting the counts for the ipsilateral (lesioned) striatum from the counts for the contralateral (un-lesioned) striatum and dividing by the average counts for the ipsilateral and contralateral striata. In order to reduce between animal variability in asymmetry ratios, a change score was calculated by subtracting the asymmetry ratio from the second PET study from the asymmetry ratio for the baseline study for each animal. Unpaired t-tests were used to compare the change in pet asymmetry ratios for the AAV-AADC and AAV-LacZ monkeys.

Figure 8A:
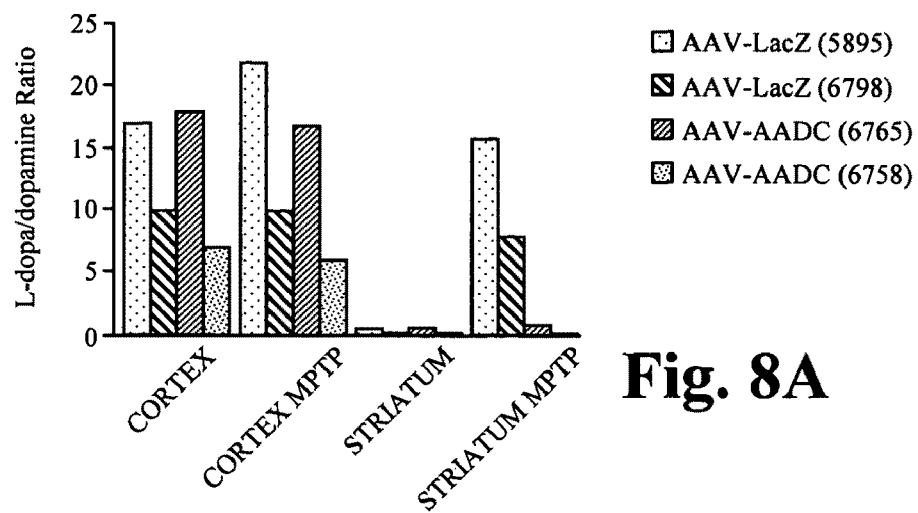
FIG. 8, panels A though C depict biochemical analysis of L-dopa levels in MPTP-lesioned monkeys. Panel A shows that L-dopa is converted to dopamine by the AACD enzyme. In cortical regions, regardless of the MPTP treatment, there is poor or no conversion of L-dopa to dopamine. Striatum is AADC-rich, therefore, most of the L-dopa has been converted to dopamine in this region. On the striatum ipsilateral to MPTP administration, L-dopa conversion to dopamine is impaired and similar to cortical activity in AAV-LacZ treated monkeys. Both AAV-AADC-treated animals show almost normal rates of L-dopa to dopamine conversion. Panel B depicts HVA analysis. HVA is a metabolite of dopamine catabolism. Since cortical regions are not able to convert L-dopa to dopamine HVA levels are low. As shown in panel A, striatum converts L-dopa to dopamine, therefore, dopamine is catabolised to HVA in this region. Since AADC activity has not been restored in the AAV-LacZ-treated monkeys HVA levels in MTPT ipsilateral striatum are low. HVA levels are significantly elevated in AAV-AADC-treated monkey in the MPTP ipsilateral striatum. Panel C shows L-dopa levels were measured in the tissue punches following L-dopa administration. Due to the different L-dopa absorption tissue levels differ between the monkeys. They are similar, however, within each subject. Tissue levels of L-dopa were dramatically reduced in the MPTP ipsilateral stratum of AAV-AADC-treated monkeys, since AADC enzyme has been restored. The activity of AADC in this region is very strong, since tissue levels of L-dopa are lower than in the contralateral striatum.
Figure 8B:
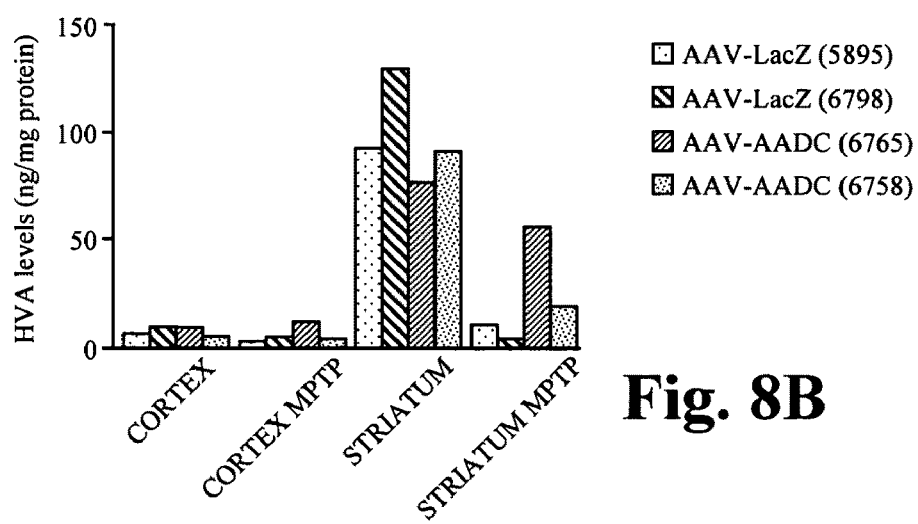
Figure 8C:
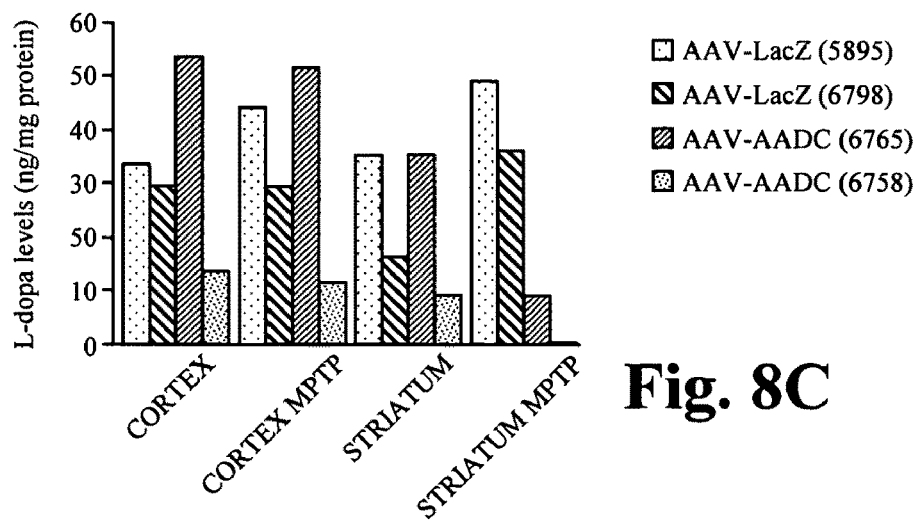
Figure 9:
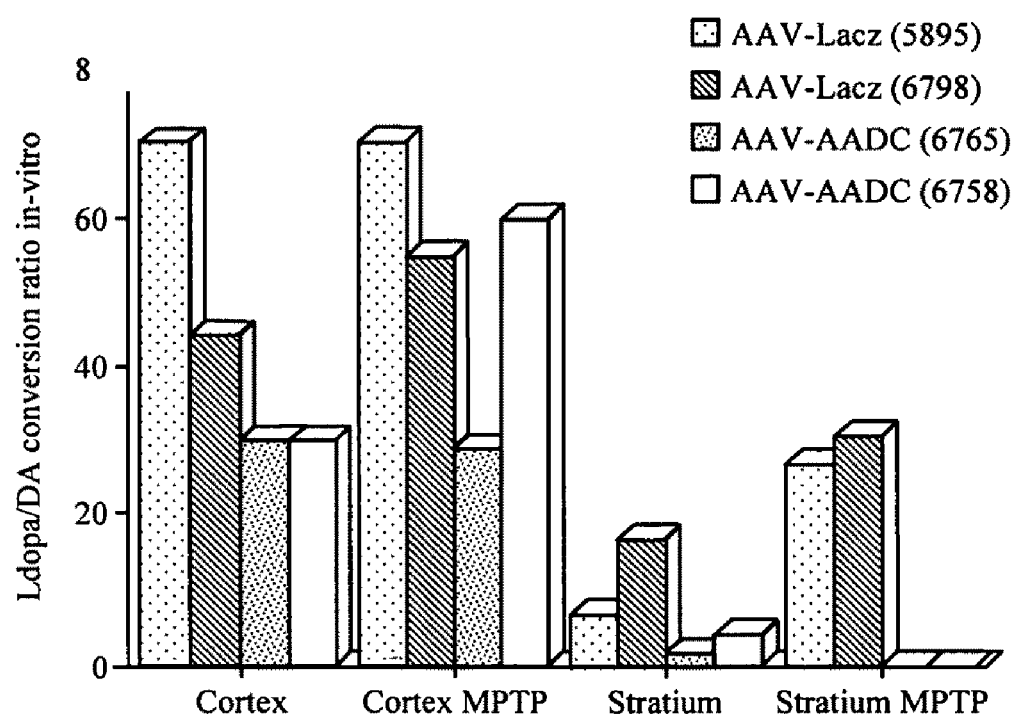
FIG. 9 is a graph depicting activity of the AADC enzyme in-vitro. Tissue punches were incubated with L-dopa as described in the material and methods. AADC enzyme activity was determined by measuring rates of L-dopa to dopamine conversion. Cortical regions contain low levels of AADC. AADC activity in contralateral striatum is high, however it is variable since there is some dopaminergic lesion on that side of the brain. AADC activity in MPTP ipsilatral striatum is significantly reduced in AAV-Lac-Z-treated monkey while it is completely restored in the AAV-DDC monkeys.

As expected, all 4 monkeys showed greater FMT uptake in the contralateral than in the ipsilateral striatum at baseline, which showed negligible uptake. At the time of the second PET study, the AAV-AADC treated monkeys showed increased FMT uptake in the ipsilateral striatum, while the AAV-LacZ treated animals showed no change from baseline. (FIG. 7). The change in FMT uptake asymmetry from baseline to the second PET study was significantly ($p<0.01$) greater for the AAV-AADC monkeys, which showed little asymmetry at the time of the second study, than for the AAV-LacZ monkeys, which showed greater contralateral FMT uptake at both time points. (FIG. 8)

Necropsy

Animals were deeply anesthetized with sodium pentobarbital (25 mg/kg i.v.) and sacrificed 8-9 weeks following AAV administration and one week following postsurgical PET scans. On the day of sacrifice, blood samples were taken, and the animals were treated with L-dopa/carbidopa preparation (Sinemet 250/25). Plasma and cervical CSF were collected and at the time of necropsy. The brains were removed 30-45 minutes following the Sinemet administration, placed in the brain matrix and sectioned coronally into 3-6 mm slices. One 3 mm thick striatal brain slice from each monkey was immediately frozen in −70° C. isopentane and stored frozen for biochemical analysis. The remaining 6 mm thick slices were post-fixed in formalin for 72 hours, washed in PBS for 12 hrs and adjusted in ascending sucrose gradient (10-20-30%) and frozen.

Histological Analysis

The formalin-fixed brain slices were cut into 30 μm thick coronal sections in a cryostat. Frozen sections were collected in series starting at the level of the rostral tip of the caudate nucleus all the way caudally to the level of the substantia nigra. Each section was saved and kept in antifreeze solution at 70° C. Serial sections were stained for tyrosine hydroxylase (TH), dopa decarboxylase (DDC) or B-galactosidese (B-gal) immunorectivity (IR). Every 12th section was washed in phosphate buffered saline (PBS) and incubated in 3% H2O2 for 20 min to block the endogenous peroxidase activity. After washing in PBS, the sections were incubated in blocking solution (10% normal horse serum for TH or 10% normal goat serum for DDC and B-gal and 0.1% Triton-X I 00 in PBS) for 30 min, followed by incubation in primary antibody solution—TH (mouse monoclonal, Chemicon, 1:1000), DDC (rabbit polygonal, Chemicon, 1:2000) or B-gal (rabbit polygonal, Cortex Blochem, 1:5000) for 24 h. The sections were then incubated for 1 h in biotinylated anti-mouse IgG secondary antibody for TH or anti-rabbit IgG secondary antibody for DDC and B-gal (Vector Labs, 1:300). The antibody binding was visualized with streptavidin horseradish peroxidase (Vector Labs, 1:300) and DAB chromogen with nickel (Vector Labs). Sections were then coverslipped and examined under a light microscope. Following tissue punching the fresh-frozen blocks were sectioned at 20 um. Sections were stained with H&E and for DDC-IR.

Quantitative estimates of the total number of AAV-infected cells within the caudate nucleus, putamen and globus pallidus were determined by using an optical dissector procedure. The optical dissector system consisted of a computer assisted image analysis system, including an Leitz Otholux 11 microscope hard-coupled to a Prior H128 computer-controlled x-y-z motorized stage, a high sensitivity Sony 3CCD video camera system (Sony, Japan) and a Macintosh G-3 computer. All analyses were performed using NeuroZoom software (La Jolla, Calif.). Prior to each series of measurements, the instrument was calibrated. The region of positive neurons in the caudate, putamen and globus pallidus was outlined at low magnification (2.5× objective). Because of the diffuse presence of AAV-infected cells within the striatum, 1% of the outlined region was measured with a systematic random design of dissector counting frames (1 505 1IM2) using a 63× plan-neofluar immersion objective with a 0.95 numerical aperture. Based on pilot experiments at least four sections equally spaced were sampled. By using the dissector principle, up to 200 AADC positive neurons were sampled by optical scanning by using uniform, systematic and random design procedures for all measurements. The average thickness of the sections was measured at 23 microns. Once the top of the section was in focus, the z-plane was lowered a 1-2 gm. Counts were than made while focusing down through three 5 lim-thick dissectors. Care was taken to ensure that the bottom forbidden plane was never included in the analysis. The volumes of the structures were calculated according to standard procedures. The total number of positive cells in the examined structures was calculated by using the formula $N=Nv \times Vs$, where Nv is the numerical density and Vs is the volume of the structure.

TH-IR staining revealed robust reduction of the nigrostriatal fibers and cell bodies in the substantia nigra on the ipsilateral side in all of the monkeys. The contralateral side showed variable reductions of TH and AADC-IR in the striatum and the substantia nigra.

DDC-IR paralleled TH-IR only in the monkeys treated with AAV-LacZ. The AAV-AADC-treated monkeys showed robust AADC staining on the ipsilateral side that exceeded staining seen on the contralateral side. A high density of AADC-IR cells was seen throughout 80% of the striatum and 100% of the globus pallidus in one of the AAV-AADC treated animals. Stereological analysis revealed 18,384 cells per $mm^3$ in the putamen, 15,126 cells per $mm^3$ in the caudate and 9,511 cells per $mm^3$ in the globus paillidus. The total number of AAV-infected cells was estimated to be at least $16 \times 10^6$ cells. In the other AAV-AADC treated monkey, AADC-IR cells were found in over 60% of the ipsilateral striatum, with 7,515 cells per $mm^3$ in the caudate and 15,352 cells per $mm^3$ in the putamen and 3,850 cells per $mm^3$ in the globus pallidus. No AADC cells were found in the contralateral striatum. The AAV/LacZ-treated monkeys did not show AADC-IR in either the ipsilateral or contralateral striata.

Cells infected with AAV appeared to have neuronal morphology. The average diameter of the infected cells was 9±2.3 μm in the putamen and 14.6±9 μm. Many Lac-Z and AADC cells had a typical medium spiny neuron morphology. AAV-infected cells were positive for the neuronal marker, Neu-N. In the AAV-AADC-treated monkeys, one out of 4-6Neu-N- positive cells was AADC-positive in the caudate and putamen, and one out of 3-4 Neu-N-positive cells was AADC positive in the globus pallidus. None of the AAV-infected cells in the Lac-Z or AADC-treated monkeys were GFAP-positive.

Areas adjacent to cannula tracts were stained with Nissl and H&E staining. No signs of cytotoxicity were observed. No perivascular cuffing was observed, regardless of the distance from the cannula. There were no signs of neuronal cell reduction close to the infusion site when compared to the contralateral side using Neu-N immunostaining. GFAP-immunostaining failed to detect any abnormal glia reaction within the AAV-treated striatum.

Biochemical Analysis

Brain regions were removed from fresh frozen blocks using a micropuncher in order to evaluate tissue levels of L-dopa and dopamine metabolites and the activity of AADC and the presence of the AAV-vector. Brain regions included striatum and cortex.

Frozen micropunches were collected, and homogenized by ultrasonic processing in 300 pl of 0.1 M perchloric acid (Fisher Scientific) containing 1% ethanol, and 0.02% EDTA (Fisher Scientific). Fifty pl of the homogenate was removed for protein analysis (BCA Protein Assay Kit Pierce #23225), and the remainder centrifuged in a mirocentrifuge for 1.5 minutes at maximum speed. 30 to 50 pl of the homogenate was used for catecholamine analysis by HPLC using an Ultrasphere C-18 ion pair, 5 p, 4.6×250 mm column (Beckman 235329); a Waters 717 plus autosampler at 4° C., Waters 510 pump at 0.9 mv,min, and amperometric electrochemical detector (Decade) set at Eox. 0.82V. The column and detector cell were set at 31° C. The mobile phase contained 2 L HPLC grade water, 2.2 g 1-heptanesulfonic acid, sodium salt (Fisher Scientific), 0.17 g EDTA, 12 ml triethylamine (Fisher Scientific), pH adjusted to 2.5 with =–8 ml 85% phosphoric acid (Fisher Scientific), and 60 ml acetonirile (J. T. Baker). The detector output was recorded and analyzed with the Waters Millennium 32 Chromatography Manager.

AADC Analysis

AADC activity was determined by an adaptation of the method of Nagatsu et al (1979) *Anal. Biochem.* 100:160-165. Briefly, tissue (10 mg/ml) was homogenized in 50 mM phosphate buffer (pH 7.4) containing 0.04 mM pyrixyl phosphate (a AADC cofactor) and 0.2 mM pargyline. Samples were pre-incubated at 37° C. for 5 minutes and the reaction was initiated by the addition of L-dopa (final concentration: 100 µM). Incubations were carried out for 20 minutes and the reaction stopped by the addition of 0.02 ml concentrated perchloric acid. After centrifugation, the supernatant dopamine concentration was determined using HPLC with electrochemical detection. (see, e.g., Boomsa et al. (1988) *Clin. Chem. Acta* 178-59-69). Protein concentration in the tissue pellet was determined using the BCA Protein Assay Kit (Pierce #23225). Results are expressed as nM/hr/mg of protein. Frozen tissue punches were processed according to standard protocols.

Cortical regions of all monkeys showed variable levels of L-dopa, however, they were consistent within each monkey. As expected, there was no decarboxylation of L-dopa to dopamine within the cortex, however, in the striatum on the side contralateral to MPTP administration, L-dopa was converted to dopamine and further metabolized to HVA. In the MPTP-treated striatum of the AAV-Lac-Z monkeys, L-dopa was not converted to dopamine, nor was it metabolized to HVA. Tissue levels of L-dopa also remained at the same levels as in the cortex in AAV-Lac-Z treated monkeys. In the MPTP-treated striatum of AAV-AADC-treated monkeys, L-dopa was converted to dopamine and HVA and tissue levels of L-dopa in this region were reduced.

AADC activity was very low in the cortical regions and in the MPTP-treated striatum of AAV-LacZ-treated monkeys. L-dopa was converted to dopamine in the contralateral striatum, suggesting high levels of AADC activity. The tissue punches from MPTP-treated striatum of AAV-AADC infected monkeys contained extremely high dopamine levels with only traces of L-dopa left.

These results demonstrate that the combination of infused AAV-AADC vector and systemic L-dopa is a promising therapy for the treatment of PD.

Thus, the invention provides a novel and efficient treatment method for CNS disorders, such as Parkinson's Disease. In addition, the invention also provides methods for determining dopamine activity in vivo.

The invention claimed is:

1. A method of increasing dopamine levels in a mammal, said method comprising:
   (a) providing a composition comprising at least $2.5 \times 10^9$ recombinant adeno-associated virus (rAAV) virions, wherein said rAAV virions comprise a transgene encoding aromatic amino acid decarboxylase (AADC); and
   (b) administering said composition directly to the brain of said mammal using a non-manual pump, to increase dopamine levels, wherein said composition is administered such that distribution of said rAAV virions is over an area greater than 5 mm$^2$.

2. The method of claim 1, wherein said pump is an infusion pump or an osmotic pump.

3. The method of claim 1, wherein said composition is administered to striatum of the brain of said mammal.

4. The method of claim 1, wherein said composition is administered under a pressure gradient.

5. The method of claim 1, wherein said composition comprises at least $2.5 \times 10^{10}$ rAAV virions.

6. The method of claim 1, wherein said mammal suffers from a central nervous system (CNS) disorder.

7. The method of claim 6, wherein said CNS disorder is Parkinson's disease.

8. The method of claim 1, further comprising administering L-dopa in said mammal.

9. The method of claim 8, wherein said L-dopa is administered by systemic administration.

10. The method of claim 9, wherein said systemic administration is oral.

11. The method of claim 8, further comprising administering carbidopa.

12. The method of claim 1, wherein at least $2.5 \times 10^{10}$ rAAV virions are administered such that distribution of said rAAV virions is over a volume of at least 250 mm$^3$.

* * * * *